(12) United States Patent
Goto et al.

(10) Patent No.: US 10,470,733 B2
(45) Date of Patent: Nov. 12, 2019

(54) X-RAY CT DEVICE AND MEDICAL INFORMATION MANAGEMENT DEVICE

(71) Applicant: Toshiba Medical Systems Corporation, Otawara-shi (JP)

(72) Inventors: Takahiro Goto, Utsunomiya (JP); Shinsuke Tsukagoshi, Nasushiobara (JP); Go Mukumoto, Obu (JP)

(73) Assignee: Canon Medical Systems Corporation, Otawara-shi (JP)

( * ) Notice: Subject to any disclaimer, the term of this patent is extended or adjusted under 35 U.S.C. 154(b) by 204 days.

(21) Appl. No.: 15/589,210

(22) Filed: May 8, 2017

(65) Prior Publication Data

US 2017/0319167 A1    Nov. 9, 2017

(30) Foreign Application Priority Data

May 9, 2016    (JP) .................................. 2016-094108
Apr. 27, 2017   (JP) .................................. 2017-088424

(51) Int. Cl.
*A61B 6/00* (2006.01)
*A61B 6/03* (2006.01)
*A61B 6/06* (2006.01)

(52) U.S. Cl.
CPC ............ *A61B 6/5211* (2013.01); *A61B 6/032* (2013.01); *A61B 6/4035* (2013.01); *A61B 6/465* (2013.01);
(Continued)

(58) Field of Classification Search
CPC ......... A61B 6/032; A61B 6/06; A61B 6/4035; A61B 6/465; A61B 6/504; A61B 6/5205;
(Continued)

(56) References Cited

U.S. PATENT DOCUMENTS

2005/0069086 A1* 3/2005 Deych .................... A61B 6/482
378/112
2007/0286332 A1   12/2007 Gohno et al.
(Continued)

FOREIGN PATENT DOCUMENTS

| JP | 2007-325853 | 12/2007 |
|----|-------------|---------|
| JP | 2008-12229  | 1/2008  |
| JP | 2011-125600 | 6/2011  |

*Primary Examiner* — Chih-Cheng Kao
(74) *Attorney, Agent, or Firm* — Oblon, McClelland, Maier & Neustadt, L.L.P.

(57) ABSTRACT

In an X-ray CT device according to an embodiment, reconstruction circuitry reconstructs a positioning image from projection data collected based on a detection signal of transmitted X-rays in positioning imaging performed at a first tube current. Circuitry detects body parts of a subject included in the positioning image. Storage stores information pieces relating to body parts, image quality levels for each of the information pieces relating to the body parts, and an X-ray count value corresponding to each of the image quality levels in an associated manner. The circuitry selects an image quality level corresponding to a desired body part. The circuitry acquires a second tube current based on the first tube current, an X-ray count value in the positioning imaging, and an X-ray count value associated with the selected image quality level. The circuitry controls an X-ray tube to perform main imaging based on the second tube current.

8 Claims, 18 Drawing Sheets

(52) U.S. Cl.
CPC ............ *A61B 6/504* (2013.01); *A61B 6/5205* (2013.01); *A61B 6/5294* (2013.01); *A61B 6/542* (2013.01); *A61B 6/545* (2013.01); *A61B 6/06* (2013.01)

(58) Field of Classification Search
CPC ..... A61B 6/5211; A61B 6/5294; A61B 6/542; A61B 6/545
See application file for complete search history.

(56) References Cited

U.S. PATENT DOCUMENTS

| | | | |
|---|---|---|---|
| 2012/0051500 A1* | 3/2012 | Johansson | A61B 6/025 378/22 |
| 2013/0108130 A1* | 5/2013 | Nukui | A61B 6/488 382/131 |

* cited by examiner

FIG.5

| IDENTIFICA-TION CODE | COORDINATES | | |
|---|---|---|---|
| | POSITIONING | SCAN | |
| | | NO-CONTRAST-ENHANCED PHASE | CONTRAST-ENHANCED PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

FIG.10

| IMAGE QUALITY LEVEL | COUNT | BENCHMARK IMAGE |
|---|---|---|
| Low Dose | a | A |
| Standard | b | B |
| Quality | c | C |
| High Quality | d | D |

FIG.15
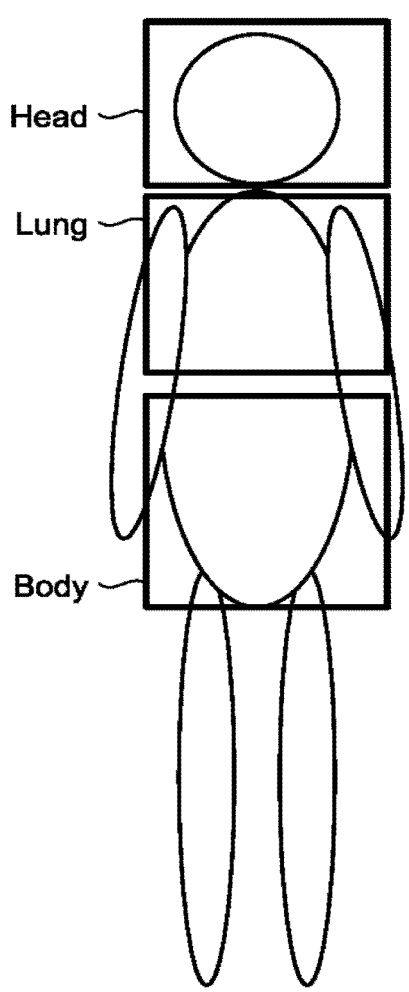
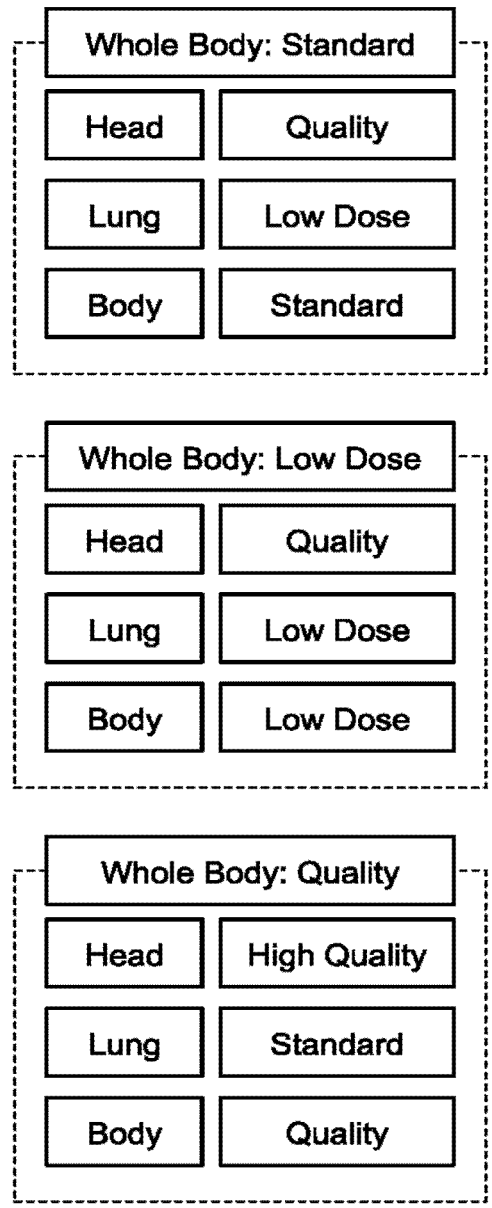

X-RAY CT DEVICE AND MEDICAL INFORMATION MANAGEMENT DEVICE

CROSS-REFERENCE TO RELATED APPLICATIONS

This application is based upon and claims the benefit of priority from Japanese Patent Application No. 2016-094108, filed on May 9, 2016 and Japanese Patent Application No. 2017-088424, filed on Apr. 27, 2017; the entire contents of which are incorporated herein by reference.

FIELD

Embodiments described herein generally relate to an X-ray CT device and a medical information management device.

BACKGROUND

In conventional imaging using an X-ray computed tomography (CT) device, imaging for positioning is performed to collect a positioning image (a scanogram) before main imaging. In imaging using an X-ray CT device, for example, auto exposure control (AEC) is performed that calculates a tube current to be supplied to the X-ray tube in main imaging based on the collected positioning image.

When calculating a tube current using the AEC, a standard deviation (SD) is used as an index of image quality. In modern reconstruction methods, however, because the relation between the tube current and the SD is non-linear, graininess and the noise power spectra (NPS) may be different from what are expected. Expected image quality is therefore less likely to be obtained.

BRIEF DESCRIPTION OF THE DRAWINGS

FIG. 5 is another illustrative drawing of exemplary body part detection processing performed by the detecting function according to the first embodiment;

FIG. 10 is a drawing to illustrate exemplary information stored in the storage according to the first embodiment;

FIG. 15 is an illustrative drawing of preset of an image quality level according to a different embodiment;

DETAILED DESCRIPTION

An X-ray CT device according to an embodiment includes an X-ray tube, a detector, an image reconstruction unit, a detecting unit, a storage unit, a selecting unit, an acquiring unit, and a control unit. The detector detects a transmitted X-ray radiated from the X-ray tube and transmitted through a subject. The image reconstruction unit reconstructs a positioning image from projection data collected in positioning imaging performed at a first tube current using a detection signal of the transmitted X-ray detected by the detector. The detecting unit detects a plurality of body parts of the subject included in the positioning image. The storage unit stores information pieces relating to the body parts, a plurality of image quality levels for each of the information pieces relating to the body parts, and information pieces relating to first X-ray count values corresponding to the respective image quality levels in a manner associated with one another. The selecting unit selects a desired body part and an image quality level corresponding to the desired body part. The acquiring unit acquires information relating to a second tube current used in main imaging based on information relating to the first tube current, information relating to a second X-ray count value used in the positioning imaging, and information relating to the first X-ray count value associated with the selected image quality level. The control unit controls the X-ray tube to perform main imaging based on the acquired second tube current.

Figure 1:
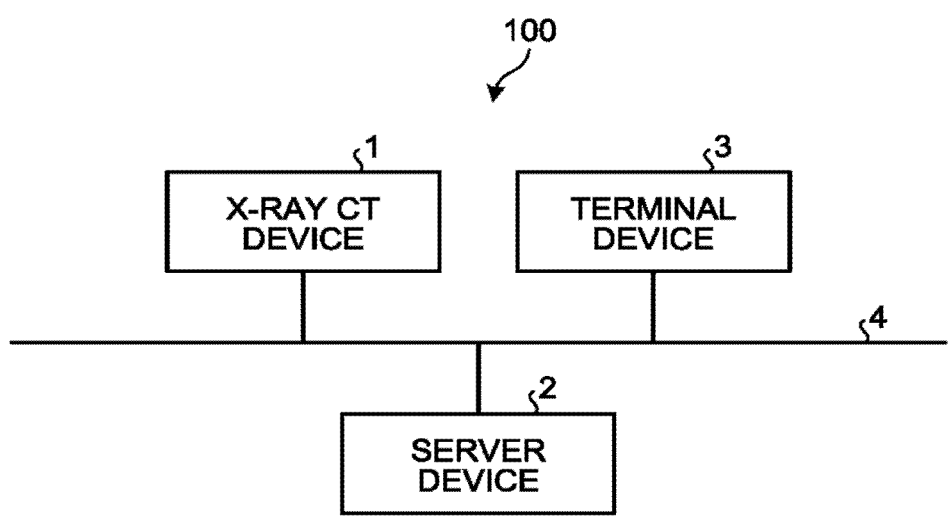
FIG. 1 is a drawing to illustrate an exemplary configuration of a medical information processing system according to a first embodiment.

The X-ray computed tomography (CT) device and a medical information management device will now be described in detail with reference to the accompanying drawings. Specifically, a medical information processing system including an X-ray CT device will be described as an example. In FIG. 1, a medical information processing system 100 includes a server device and a terminal device; however, the medical information processing system 100 can actually include a plurality of server devices and terminal devices. The medical information processing system 100 can further include a medical image diagnostic device such as an X-ray diagnostic device, a magnetic resonance imaging (MRI) device, and an ultrasonic diagnostic device.

First Embodiment

FIG. 1 is a drawing to illustrate an exemplary configuration of the medical information processing system 100 according to the first embodiment. As illustrated in FIG. 1, the medical information processing system 100 according to the first embodiment includes an X-ray CT device 1, a server device 2, and a terminal device 3. The X-ray CT device 1, the server device 2, and the terminal device 3 are directly or indirectly communicable with one another using, for example, an in-hospital local area network (LAN) 4 deployed in the hospital. For example, when a picture archiving and communication system (PACS) is installed in the medical information processing system 100, the devices transmit and receive medical images and the like to and from one another in accordance with the digital imaging and communications in medicine (DICOM) standard.

Furthermore, a hospital information system (HIS), a radiology information system (RIS), and others are further installed in the medical information processing system 100 for management of various kinds of information. For example, the terminal device 3 transmits an examination order formed along the above-described systems to the X-ray CT device 1 and the server device 2. The X-ray CT device 1 acquires patient information from the examination order directly received from the terminal device 3 or a patient list (a modality work list) in each modality created by the server device 2 receiving the examination order and collects X-ray CT image data for each patient. The X-ray CT device 1 transmits collected X-ray CT image data and image data generated by providing various kinds of image processing on the X-ray CT image data to the server device 2. The server device 2 stores the X-ray CT image data and the image data received from the X-ray CT device 1, generates image data from the X-ray CT image data, and transmits image data upon a request of acquiring from the terminal device 3 to the terminal device 3. The terminal device 3 displays the image data received from the server device 2 on a monitor and the like. Each device will now be described.

The terminal device 3 is a device set up in each department in the hospital and operated by doctors working in the department. Examples of the terminal device 3 include a personal computer (PC), a tablet PC, a personal digital assistant (PDA), and a mobile phone. For example, chart information including symptoms of a patient and findings of the doctor are input in the terminal device 3 by each doctor. Furthermore, an examination order for ordering an examination using the X-ray CT device 1 is input to the terminal device 3, and the terminal device 3 transmits the input examination order to the X-ray CT device 1 and the server device 2. In other words, a doctor in a department operates the terminal device 3, reads reception information and electrical chart information of a patient visiting the hospital, examines the patient, and inputs chart information in the read electrical chart. The doctor in the department further transmits an examination order by operating the terminal device 3 upon necessity of an examination using the X-ray CT device 1.

The server device 2 is a device storing medical images (for example, X-ray CT image data collected by the X-ray CT device 1 and image data) collected by a medical image diagnostic device and providing various kinds of image processing on the medical images. Examples of the server device 2 include a PACS server. For example, the server device 2 receives a plurality of examination orders from the terminal device 3 installed in each department, creates a patient list for each medical image diagnostic device, and transmits the created patient list to the corresponding medical image diagnostic device. For example, the server device 2 receives an examination order ordering an examination using the X-ray CT device 1 from the terminal device 3 in each department, creates a patient list, and transmits the created patient list to the X-ray CT device 1. The server device 2 stores X-ray CT image data collected by the X-ray CT device 1 and image data and transmits the X-ray CT image data and the image data to the terminal device 3 upon request of acquiring from the terminal device 3.

Figure 2:
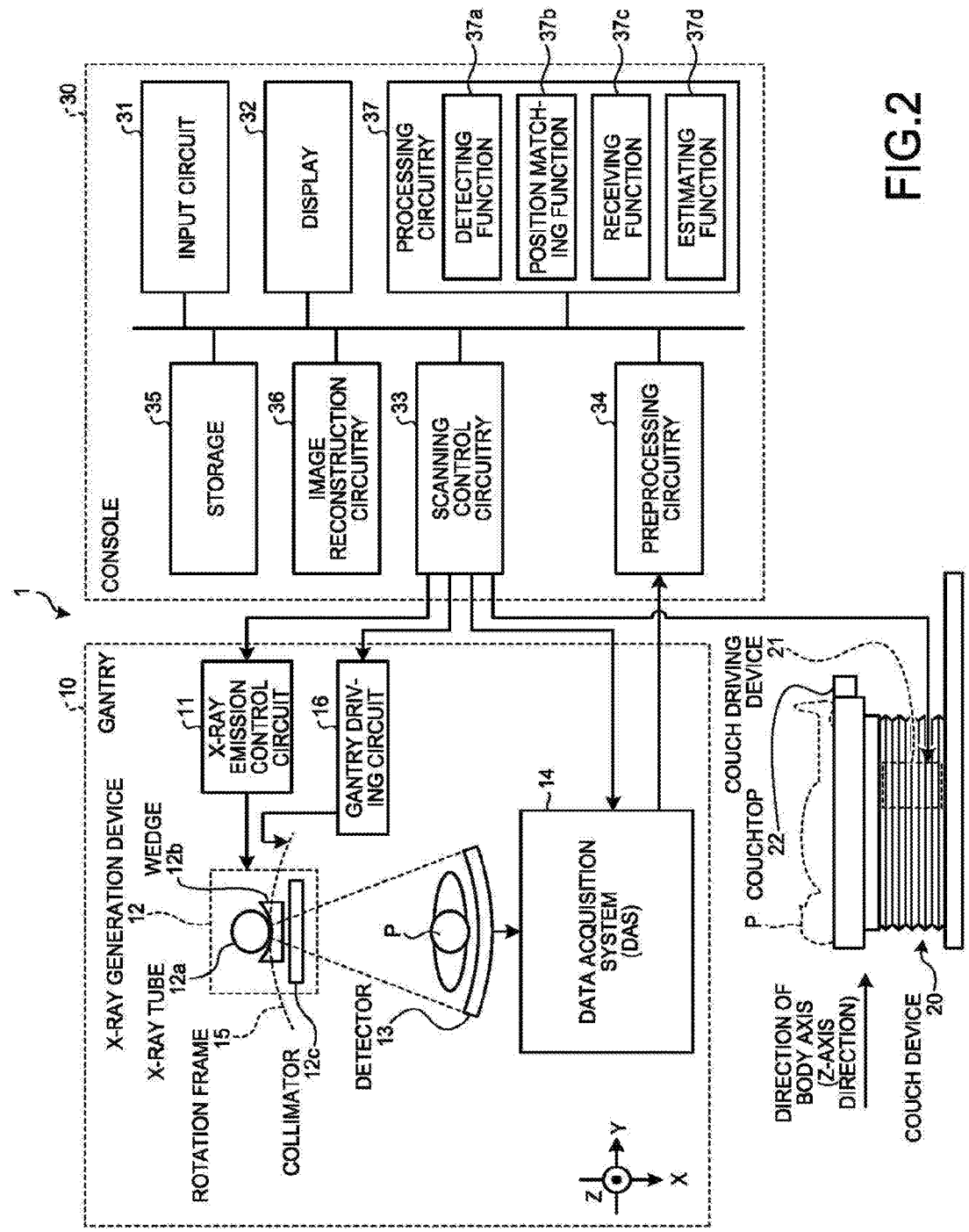
FIG. 2 is a drawing to illustrate an exemplary configuration of an X-ray CT device according to the first embodiment.

The X-ray CT device 1 collects X-ray CT image data of each patient and transmits the collected X-ray CT image data and image data generated by providing various kinds of image processing on the X-ray CT image data to the server device 2. FIG. 2 is a drawing to illustrate an exemplary configuration of the X-ray CT device 1 according to the first embodiment. As illustrated in FIG. 2, the X-ray CT device 1 according to the first embodiment includes a gantry 10, a couch device 20, and a console 30.

The gantry 10 is a device irradiating a subject P (a patient) with X-rays, detecting the X-rays transmitted through the subject P, and outputting the detection result to the console 30. The gantry 10 includes an X-ray emission control circuit 11, an X-ray generation device 12, a detector 13, a data acquisition system (DAS) 14, a rotation frame 15, and a gantry driving circuit 16.

The rotation frame 15 is a circular frame supporting the X-ray generation device 12 and the detector 13 in a manner opposite to each other with the subject P placed therebetween and rotated at a high speed on a circular path having the subject P as its center by the later-described gantry driving circuit 16.

The X-ray emission control circuit 11 is a device serving as a high voltage generator and supplying high voltage to an X-ray tube 12a. The X-ray tube 12a generates X-rays using the high voltage supplied from the X-ray emission control circuit 11. The X-ray emission control circuit 11 adjusts the amount of X-ray emitted on the subject P by adjusting tube voltage and a tube current supplied to the X-ray tube 12a under control of later-described scanning control circuitry 33.

The X-ray emission control circuit 11 switches a wedge 12b. The X-ray emission control circuit 11 adjusts the emission range (the fan angle and the cone angle) of X-rays by adjusting the amount of opening of a collimator 12c. In this embodiment, a plurality of kinds of wedges may be manually switched by an operator.

The X-ray generation device 12 is a device generating an X-ray and irradiating the subject P with the generated X-ray and includes the X-ray tube 12a, the wedge 12b, and the collimator 12c.

The X-ray tube 12a is a vacuum tube irradiating the subject P with X-ray beams using high voltage supplied from a high voltage generator (not illustrated) and irradiating the subject P with the X-ray beams with rotation of the rotation frame 15. The X-ray tube 12a generates X-ray beams radiating with a fan angle and a cone angle. For example, the X-ray tube 12a is capable of continuously radiating X-rays around the entire circumference of the subject P for full reconstruction and capable of continuously radiating X-rays in a range (180 degrees+the fan angle) of radiation enabling half reconstruction for half reconstruction under control of the X-ray emission control circuit 11.

Furthermore, under control of the X-ray emission control circuit 11, the X-ray tube 12a is capable of intermittently radiating X-rays (pulse X-rays) at a predetermined position (at the position of an X-ray tube). The X-ray emission control circuit 11 is capable of modulating the intensity of X-rays radiated from the X-ray tube 12a. For example, the X-ray emission control circuit 11 increases the intensity of X-rays radiated from the X-ray tube 12a at a specific position of the X-ray tube and decreases the intensity of X-rays radiated from the X-ray tube 12a in a range excluding the specific X-ray tube position.

The wedge 12b is an X-ray filter for adjusting the amount of X-ray radiated from the X-ray tube 12a. Specifically, the wedge 12b is a filter transmitting and attenuating X-rays radiated from the X-ray tube 12a such that the X-rays emitted on the subject P from the X-ray tube 12a have predetermined distribution. Examples of the wedge 12b include a filter made of aluminum in a manner having a specific target angle and a specific thickness. The wedge 12b may be referred to as a wedge filter and a bow-tie filter.

The collimator 12c is a slit for limiting the emission range of X-rays the amount of which is adjusted by the wedge 12b under control of the X-ray emission control circuit 11.

The gantry driving circuit 16 swivels the X-ray generation device 12 and the detector 13 on the circular path having the subject P as its center by driving and rotating the rotation frame 15.

The detector 13 is a two-dimensional array detector (a plane detector) detecting X-rays transmitted through the subject P, and a plurality of rows of detecting elements including X-ray detecting elements for a plurality of channels are aligned along the direction of the body axis (the direction of the Z-axis in FIG. 2) of the subject P. More specifically, the detector 13 in the first embodiment has X-ray detecting elements aligned in a plurality of rows such as 320 rows along the direction of the body axis of the subject P and is capable of detecting X-rays transmitted through the subject P in a wider range such as a range including the lungs and the heart of the subject P. In other words, the detector 13 detects X-rays emitted from the X-ray tube 12a and transmitted through the subject.

The data acquisition system 14, which is a DAS, collects projection data from detection data of X-rays detected by the detector 13. For example, the data acquisition system 14 generates projection data by providing amplification processing, analogue-to-digital conversion processing, sensitivity correction processing between channels, and the like on X-ray intensity distribution data detected by the detector 13 and transmits the generated projection data to the later-described console 30. For example, when X-rays are continuously radiated from the X-ray tube 12a during rotation of the rotation frame 15, the data acquisition system 14 collects projection data group corresponding to the entire circumference (360 degrees). The data acquisition system 14 further associates each collected projection data piece with the position of the X-ray tube and transmits the data to the later-described console 30. The position of the X-ray tube serves as information indicating a projection direction of projection data. The sensitivity correction processing between channels may be performed by later-described preprocessing circuitry 34.

The couch device 20 is a device where the subject P is laid and includes a couch driving device 21 and a couchtop 22 as illustrated in FIG. 2. The couch driving device 21 moves the couchtop 22 in the Z-axis direction and moves the subject P into the rotation frame 15. The couchtop 22 is a board where the subject P is laid.

The gantry 10 performs, for example, helical scanning that helically scans the subject P by rotating the rotation frame 15 while moving the couchtop 22. The gantry 10 further performs conventional scanning that moves the couchtop 22 and scans the subject P on a circular path by rotating the rotation frame 15 with the position of the subject P fixed. The gantry 10 further applies a step-and-shoot approach that moves the position of the couchtop 22 at regular intervals and performs conventional scanning in a plurality of scanning areas.

The console 30 is a device that receives operations on the X-ray CT device 1 from an operator and reconstructs X-ray CT image data using projection data collected by the gantry 10. As illustrated in FIG. 2, the console 30 includes an input circuit 31, a display 32, the scanning control circuitry 33, the preprocessing circuitry 34, storage 35, image reconstruction circuitry 36, and processing circuitry 37.

The input circuit 31 has a mouse, a keyboard, a truck ball, a switch, a button, a joystick, or the like used by an operator of the X-ray CT device 1 for inputting various kinds of instructions and various kinds of settings and forwards the instructions and information relating to the settings received from the operator to the processing circuitry 37. For example, the input circuit 31 receives conditions of imaging the X-ray CT image data, conditions of reconstructing the X-ray CT image data, conditions of providing image processing on the X-ray CT image data, and the like from the operator. The input circuit 31 receives an operation for selecting an examination performed on the subject P. The input circuit 31 further receives an operation for designating a certain body part on the image.

The display 32 is a monitor referred to by an operator. Under control of the processing circuitry 37, the display 32 displays image data generated from the X-ray CT image data to the operator and displays a graphical user interface (GUI) for receiving various kinds of instructions and various kinds of settings from the operator through the input circuit 31. The display 32 further displays, for example, a scan plan creating screen and a screen of ongoing scanning. The display 32 further displays a virtual patient image, image data, and the like including information relating to radiation exposure. The virtual patient image displayed by the display 32 will be described later in detail.

Under control of the processing circuitry 37, the scanning control circuitry 33 controls processing of collecting projection data on the gantry 10 by controlling operations of the X-ray emission control circuit 11, the gantry driving circuit 16, the data acquisition system 14, and the couch driving device 21. More specifically, the scanning control circuitry 33 controls processing of collecting projection data in positioning imaging for collecting positioning images (scanograms) and in main imaging (main scan) for collecting diagnostic images. The X-ray CT device 1 according to the first embodiment is capable of imaging a two-dimensional scanogram and a three-dimensional scanogram.

The scanning control circuitry 33 images two-dimensional scanograms by continuously taking images while moving the couchtop at a constant speed with the X-ray tube 12a fixed to a position of the zero degree (a position facing the subject). In another manner, the scanning control circuitry 33 images two-dimensional scanograms by intermittently moving the couchtop and intermittently repeatedly taking images in a manner synchronous with the move of the couchtop with the X-ray tube 12a fixed at a position of the zero degree. The scanning control circuitry 33 is capable of taking positioning images from any direction (for example, from a lateral direction) other than from the direction facing the subject.

Figure 3:
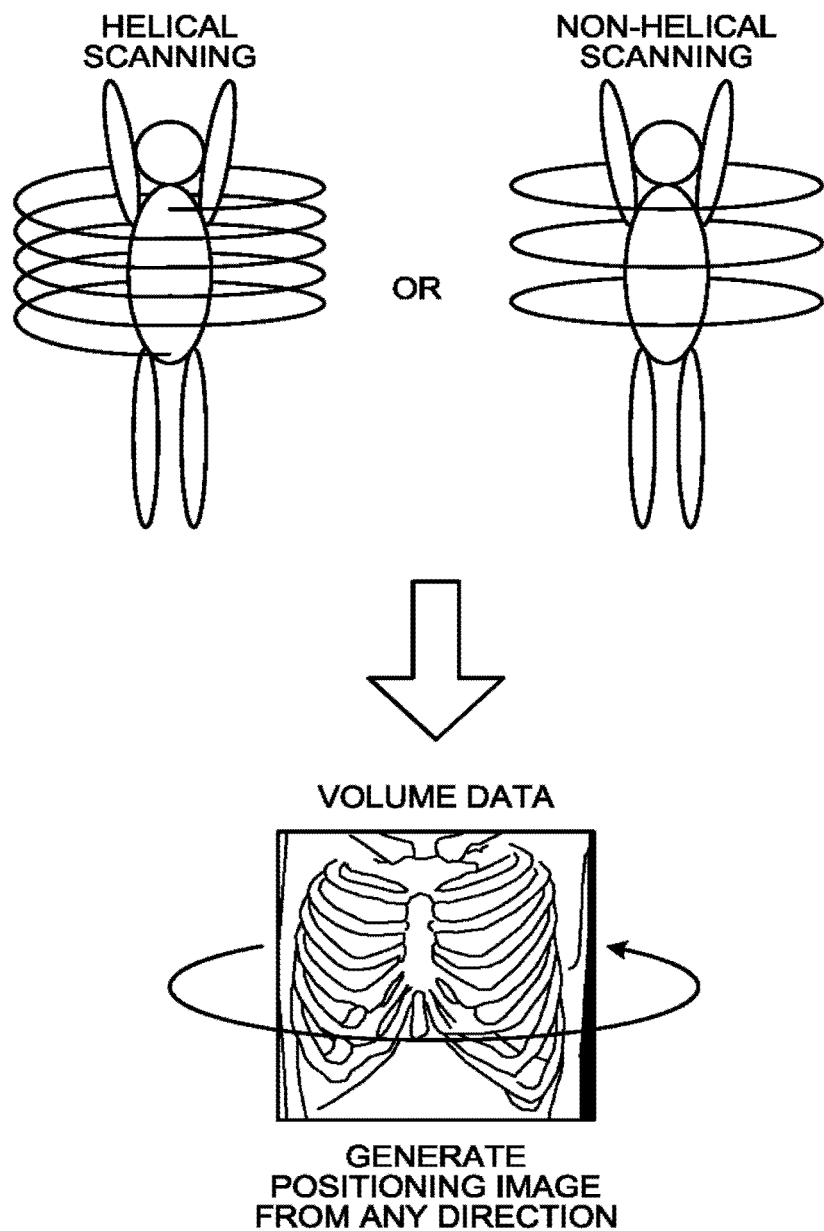
FIG. 3 is an illustrative drawing of three-dimensional scanography by scanning control circuitry according to the first embodiment.

The scanning control circuitry 33 images three-dimensional scanograms by collecting projection data corresponding to the entire circumference of the subject. FIG. 3 is an illustrative drawing of three-dimensional scanography by the scanning control circuitry 33 according to the first embodiment. For example, as illustrated in FIG. 3, the scanning control circuitry 33 collects projection data corresponding to the entire circumference of the subject using helical scanning or non-helical scanning. The scanning control circuitry 33 performs helical scanning or non-helical scanning on a wide range such as the entire chest, the entire abdomen, the entire upper body, and the entire body of the subject at a lower dose than that in main imaging. For example, scanning using the above-described step-and-shoot approach is performed in the non-helical scanning.

In this manner, with the scanning control circuitry 33 collecting projection data corresponding to the entire circumference of the subject, the later-described image reconstruction circuitry 36 can reconstruct three-dimensional X-ray CT image data (volume data), and a positioning image can be generated from any direction using the reconstructed volume data as illustrated in FIG. 3. Whether the positioning image is taken in a two-dimensional manner or a three-dimensional manner may be optionally determined by an operator or may be predetermined according to the content of the examination.

Referring back to FIG. 2, the preprocessing circuitry 34 provides logarithmic transformation processing and correction processing such as offset correction, sensitivity correction, and beam hardening correction on projection data generated by the data acquisition system 14 and generates corrected projection data. More specifically, the preprocessing circuitry 34 generates corrected projection data for the projection data of a positioning image generated by the data acquisition system 14 and for the projection data collected in main imaging and stores the corrected projection data pieces in the storage 35.

The storage 35 stores the projection data pieces generated by the preprocessing circuitry 34. More specifically, the storage 35 stores projection data of a positioning image and projection data of a diagnostic image collected in main imaging, which are generated by the preprocessing circuitry 34. The storage 35 stores image data generated by the later-described image reconstruction circuitry 36 and a virtual patient image. The storage 35 further stores a result of processing performed by the later-described processing circuitry 37 as appropriate. The virtual patient image and a result of processing performed by the processing circuitry 37 will be later described.

The image reconstruction circuitry 36 reconstructs X-ray CT image data using projection data stored by the storage 35. More specifically, the image reconstruction circuitry 36 reconstructs X-ray CT image data from the projection data of a positioning image and from the projection data of a diagnostic image. Various reconstruction methods including, for example, back projection processing are applicable. Filtered back projection (FBP) is an exemplary method of back projection processing. In another manner, the image reconstruction circuitry 36 can reconstruct X-ray CT image data using the iterative reconstruction. In other words, the image reconstruction circuitry 36 reconstructs a positioning image from projection data collected based on a detection signal of transmitted X-rays from the detector 13 in positioning imaging performed at the first tube current. The image reconstruction circuitry 36 is an example of an image reconstruction unit.

The image reconstruction circuitry 36 generates image data by providing various kinds of image processing on X-ray CT image data and stores reconstructed X-ray CT image data and image data generated by various kinds of image processing in the storage 35.

The processing circuitry 37 provides overall control on the X-ray CT device 1 by controlling operations of the gantry 10, the couch device 20, and the console 30. Specifically, the processing circuitry 37 controls CT scanning performed in the gantry 10 by controlling the scanning control circuitry 33. The processing circuitry 37 controls the console 30 to perform image reconstruction processing and image generation processing by controlling the image reconstruction circuitry 36 and controls the display 32 to display various kinds of image data stored by the storage 35.

Furthermore, as illustrated in FIG. 2, the processing circuitry 37 executes a detecting function 37a, a position matching function 37b, a receiving function 37c, and an estimating function 37d. For example, the processing function executed by each of the detecting function 37a, the position matching function 37b, the receiving function 37c, and the estimating function 37d, which are components of the processing circuitry 37 illustrated in FIG. 2, is stored in the storage 35 as a computer-executable program. The processing circuitry 37 is a processor implementing functions corresponding to respective programs by reading the programs from the storage 35 and executing the programs. In other words, the processing circuitry 37 having read programs includes respective functions illustrated in the processing circuitry 37 in FIG. 2. The processing circuitry 37 is an example of a control unit, and the detecting function 37a is an example of a detecting unit.

The detecting function 37a detects a plurality of body parts on the subject included in three-dimensional image data. Specifically, the detecting function 37a detects body parts such as organs included in three-dimensional X-ray CT image data (volume data) reconstructed by the image reconstruction circuitry 36. For example, the detecting function 37a detects body parts such as organs from at least one of the volume data piece of a positioning image or the volume data piece of a diagnostic image based on anatomical landmarks. The anatomical landmark is a point indicative of a characteristic of a body part such as a specific bone, an organ, a blood vessel, a nerve, and an inner cavity. The detecting function 37a detects a bone, an organ, a blood vessel, a nerve, an inner cavity, and others included in the volume data by detecting anatomical landmarks of a specific organ, a bone, and the like. The detecting function 37a is further capable of detecting positions of a head, a neck, a chest, an abdomen, legs, and others included in the volume data by detecting landmarks characteristic in a human body. Body parts described in this embodiment include a bone, an organ, a nerve, an inner cavity, and the like, and the positions thereof. Exemplary detection of a body part by the detecting function 37a will now be described.

For example, the detecting function 37a extracts an anatomical landmark from a voxel value included in volume data of a positioning image or in volume data of a diagnostic image. A detecting function 61 removes inaccurate landmarks from among landmarks extracted from the volume data by comparing a three-dimensional position of the anatomical landmark according to information such as a textbook with the position of the landmark extracted from the volume data and optimizes positions of the landmarks extracted from the volume data. In this manner, the detecting function 61 detects body parts of the subject included in volume data. For example, the detecting function 37a extracts anatomical landmarks included in volume data using a supervised machine learning algorithm. The above-described supervised machine learning algorithm is constructed using a plurality of supervised images in which correct anatomical landmarks are manually placed. In this case, for example, a decision forest is used.

The detecting function 37a compares a model indicating three-dimensional positional relation between anatomical landmarks on a body with the extracted landmark and optimizes the extracted landmark. The above-described model is constructed using the above-described supervised image. For example, a point distribution model is used. The detecting function 37a removes inaccurate landmarks by comparing a model defining the shape of a body part, positional relation of the body part, a distinctive point of the body part, and the like based on a plurality of supervised images in which correct anatomical landmarks are manually placed with each extracted landmark and optimizes the landmarks.

Figure 4A:
FIG. 4A and FIG. 4B are illustrative drawings of exemplary body part detection processing performed by a detecting function according to the first embodiment.
Figure 4B:
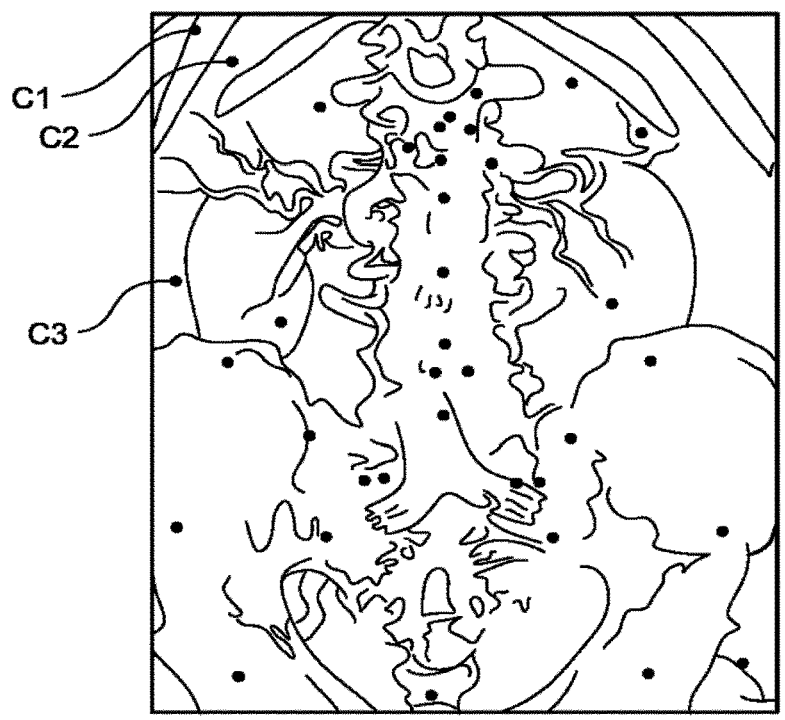

Exemplary body part detection processing performed by the detecting function 37a will now be described with reference to FIGS. 4A, 4B, 5, and 6. FIGS. 4A, 4B, 5, and 6 are illustrative drawings of exemplary body part detection processing performed by the detecting function 37a according to the first embodiment. Landmarks are two-dimensionally arranged in FIGS. 4A and 4B; however the landmarks are actually arranged in three dimensions. For example, as illustrated in FIG. 4A, the detecting function 37a extracts voxels regarded as anatomical landmarks (the black circles in FIG. 4A) by applying a supervised machine learning algorithm to volume data. As illustrated in FIG. 4B, the detecting function 37a thereafter removes inaccurate landmarks from among the extracted voxels by fitting the positions of the extracted voxels to a model defining the shape of a body part, positional relation of the body part, a distinctive point of the body part, and the like and extracts voxels corresponding to more accurate landmarks.

The detecting function 37a adds an identification code for identifying a landmark indicative of a characteristic of the body part to the extracted landmark (voxel) and stores information in which the identification code is associated with positional information (coordinates) of the landmark in the storage 35 in a manner accompanying the image data. For example, the detecting function 37a assigns identification codes such as C1, C2, and C3 to the extracted landmarks (voxels) as illustrated in FIG. 4B. The detecting function 61 has each data piece on which the detection processing has been performed accompanied by the identification codes and stores the data in the storage 35. More specifically, the detecting function 61 detects a body part of the subject included in volume data reconstructed from at least one of projection data piece of a positioning image, projection data piece collected without contrast enhancement, and projection data piece collected with the contrast enhanced by a contrast agent.

For example, as illustrated in FIG. 5, the detecting function 37a associates coordinates of each voxel detected from volume data (Positioning in FIG. 5) of a positioning image with an identification code and stores the information in the storage 35 in a manner accompanying the volume data. For example, the detecting function 37a extracts coordinates of a marker from volume data of a positioning image and stores information such as "the identification code: C1, coordinates $(x_1, y_1, z_1)$" and "the identification code: C2, coordinates $(x_2, y_2, z_2)$" in a manner associated with the volume data as illustrated in FIG. 5. With this process, the detecting function 37a is capable of identifying what kind of landmark is located at which position in volume data of a positioning image and detecting a body part such as an organ based on the information.

Furthermore, as illustrated in FIG. 5, the detecting function 61 stores information in which coordinates of each voxel detected from volume data (Scan in FIG. 5) of a diagnostic image are associated with an identification code in the storage 35 in a manner accompanying the volume data, for example. The detecting function 61 is further capable of extracting coordinates of a marker from each of a volume data piece (Contrast-enhanced phase in FIG. 5) with the contrast enhanced by a contrast agent and a volume data piece (No-contrast-enhanced phase in FIG. 5) with no contrast enhanced by a contrast agent in scanning and associating the extracted coordinates with an identification code.

For example, the detecting function 61 extracts coordinates of a marker from the volume data in the no-contrast-enhanced phase of volume data pieces of diagnostic images and stores information such as "the identification code: C1, coordinates $(x'_1, y'_1, z'_1)$" and "the identification code: C2, coordinates $(x'_2, y'_2, z'_2)$" as illustrated in FIG. 5 in a manner associated with the volume data. Furthermore, the detecting function 61 extracts coordinates of a marker from the volume data in the contrast-enhanced phase of volume data pieces of diagnostic images and stores information such as "the identification code: C1, coordinates $(x'_1, y'_1, z'_1)$" and "the identification code: C2, coordinates $(x'_2, y'_2, z'_2)$" as illustrated in FIG. 5 in a manner associated with the volume data. In this case, when extracting markers from the volume data in the contrast-enhanced phase, such a marker is included that turns to be extractable by undergoing contrast enhancement. For example, when extracting markers from the volume data in the contrast-enhanced phase, the detecting function 61 is capable of extracting a blood vessel and the like having the contrast enhanced by a contrast agent. As illustrated in FIG. 5, for the volume data in the contrast-enhanced phase, the detecting function 61 therefore associates coordinates, for example, $(x'_{31}, Y'_{31}, z'_{31})$ to $(x'_{34}, y'_{34}, z'_{34})$, of a marker of a blood vessel and the like extracted by undergoing contrast enhancement with an identification code such as C31, C32, C33, and C34 for identifying the blood vessel.

As described above, the detecting function 61 is capable of identifying what kind of marker is located at which position in the volume data of a positioning image or the volume data of a diagnostic image and detecting a body part such as an organ based on the information. For example, the detecting function 37a detects the position of a target body part to be detected using information relating to anatomical positional relation between the target body part and a body part around the target body part. For example, in the case with "lungs" as the target body part, the detecting function 37a acquires coordinate information associated with an identification code indicative of a characteristic of the "lungs" and further acquires coordinate information associated with identification codes indicative of body parts around the "lungs" such as the "ribs", the "clavicles", the "heart", and the "diaphragm". The detecting function 37a thereafter extracts a region of the "lungs" in the volume data using information relating to anatomical positional relation between the "lungs" and other body parts around the "lungs" and the acquired coordinate information.

Figure 6:
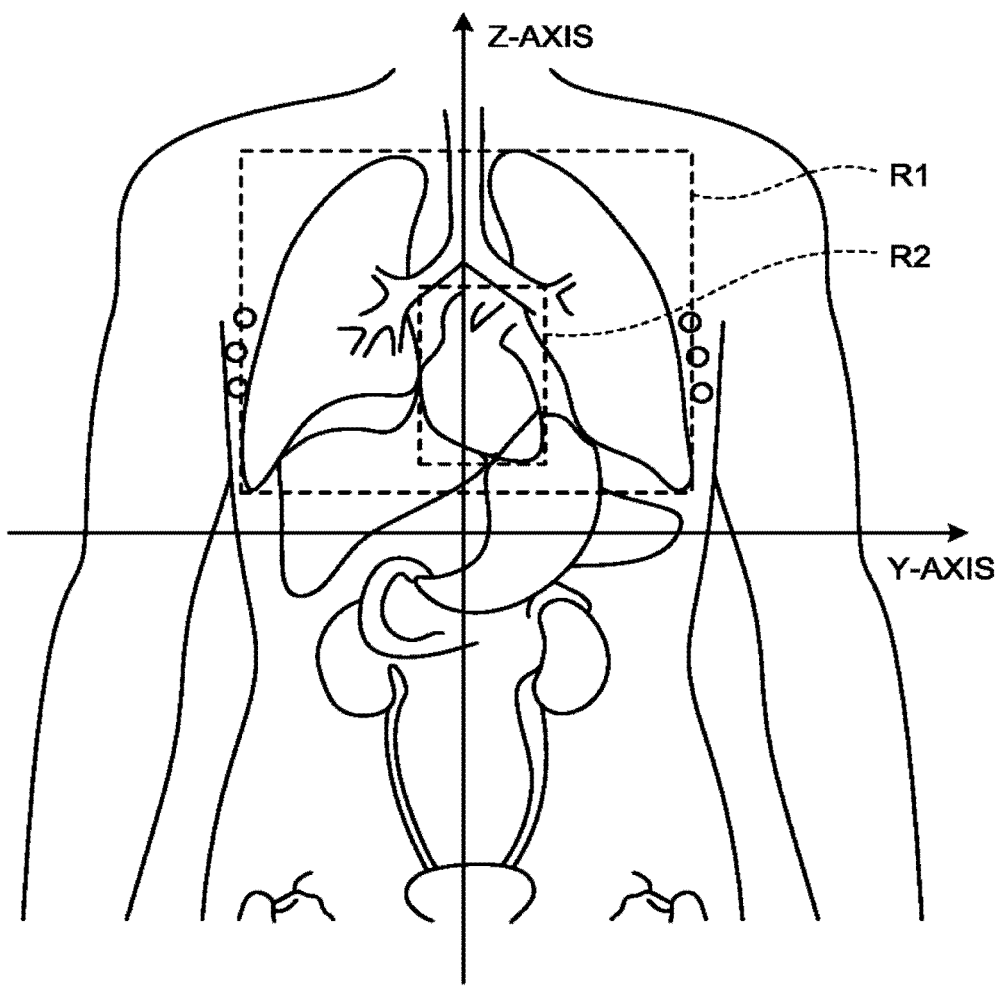
FIG. 6 is still another illustrative drawing of exemplary body part detection processing performed by the detecting function according to the first embodiment.

For example, as illustrated in FIG. 6, the detecting function 37a extracts a region R1 corresponding to the "lungs" in the volume data based on information relating to positional relation such as "the apex of the lung: two to three centimeters above from the clavicles" and "the lower ends of the lungs: the level of the seventh rib" and coordinate information of each body part. The detecting function 37a extracts coordinate information of voxels in the region R1 in the volume data. The detecting function 37a thereafter associates the extracted coordinate information with information of the body part and stores the information in the storage 35 in a manner accompanying the volume data. Similarly, as illustrated in FIG. 6, the detecting function 37a is capable of extracting, for example, a region R2 corresponding to the "heart" in the volume data.

The detecting function 37a detects positions included in volume data based on landmarks defining positions of the head, the chest, and the like of a human body. Any position of a body part of a human body such as the head and the chest can be defined. For example, when the area from the seventh cervical spine to the lower ends of the lungs is defined as a chest, the detecting function 37a detects the area from a landmark corresponding to the seventh cervical spine to landmarks corresponding to the lower ends of the lungs as a chest. The detecting function 37a is capable of detecting body parts using various methods other than the above-described method using anatomical landmarks. For example, the detecting function 37a is capable of detecting body parts included in volume data using, for example, the region growing method based on voxel values. In other words, the detecting function 37a is an example of a detecting unit that detects a plurality of body parts of a subject included in a positioning image.

The position matching function 37b matches a position of each body part of the subject included in three-dimensional image data with a position of each body part of a human body included in virtual patient data. The virtual patient data is information indicating a benchmark position of each body part of a human body. The position matching function 37b matches a body part of the subject with a benchmark position of the body part and stores the matching result in the storage 35. For example, the position matching function 37b matches a virtual patient image in which body parts of a human body are arranged at respective benchmark positions with volume data of the subject.

A virtual patient image is now described. A virtual patient image is preliminarily generated as an X-ray image of an actual human body, for example, in a standard body type, which is determined based on a plurality of combinations of parameters relating to a body type such as the age, an adult or a child, a male or a female, the weight, and the height and is stored in the storage 35. The storage 35 stores data of a plurality of virtual patient images corresponding to the above-described combinations of parameters. In this process, the storage 35 stores the virtual patient image in a manner associated with anatomical landmarks (characteristics). For example, a human body has numerous anatomical landmarks, which can be relatively easily extracted from an image using image processing such as pattern recognition based on the morphological characteristics and the like of the body. Positions and arrangement of the numerous anatomical landmarks on the body are roughly determined according to the age, an adult or a child, a male or a female, and the body type including the weight and the height, and others.

Figure 7:
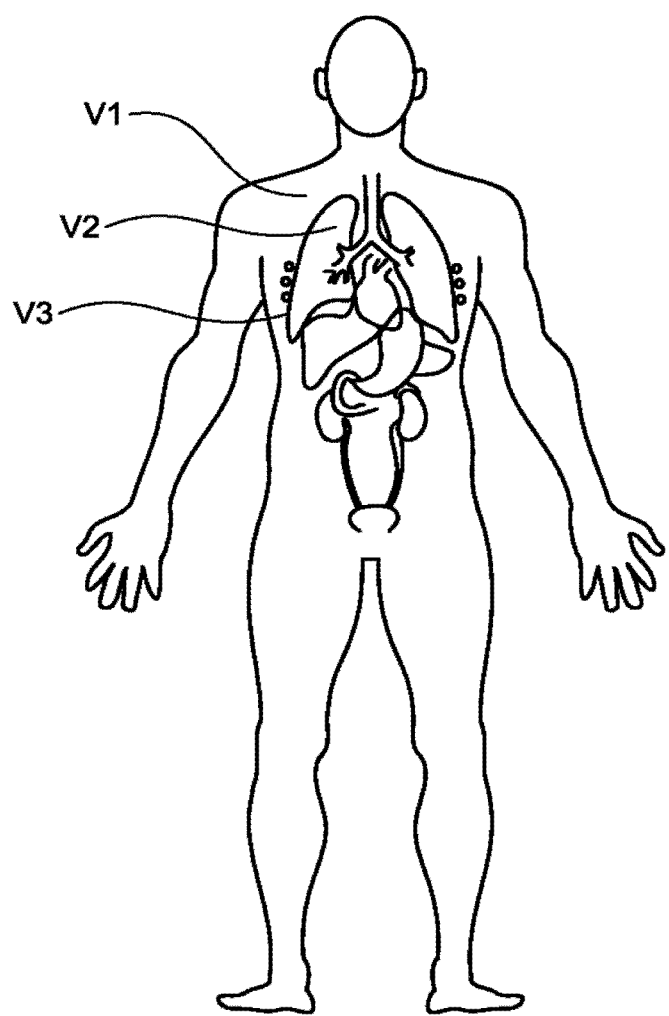
FIG. 7 is a drawing to illustrate an exemplary virtual patient image stored by storage according to the first embodiment.

The numerous anatomical landmarks are preliminarily detected from the virtual patient image stored by the storage 35. Positional data of the detected landmarks and identification codes of the respective landmarks are stored in a manner accompanying or associated with data of the virtual patient image. FIG. 7 is a drawing to illustrate an exemplary virtual patient image stored by the storage 35 according to the first embodiment. For example, as illustrated in FIG. 7, the storage 35 stores a virtual patient image on which anatomical landmarks and identification codes such as "V1", "V2", and "V3" for identifying the respective landmarks are associated with a three-dimensional human body including body parts such as organs.

The storage 35 stores coordinates of a landmark on the coordinate space of a three-dimensional human body and a corresponding identification code in a manner associated with each other. For example, the storage 35 stores coordinates of a landmark corresponding to the identification code "V1" illustrated in FIG. 7 in an associated manner. Similarly, the storage 35 stores an identification code and coordinates of a landmark in a manner associated with each other. FIG. 7 illustrates the lungs, the heart, the liver, the stomach, and the kidneys as organs; however, other numerous organs, bones, blood vessels, nerves, and the like are included in the actual virtual patient image. Furthermore, FIG. 7 illustrates landmarks corresponding to the identification codes "V1", "V2", and "V3"; however, further numerous landmarks are actually included.

Figure 8:
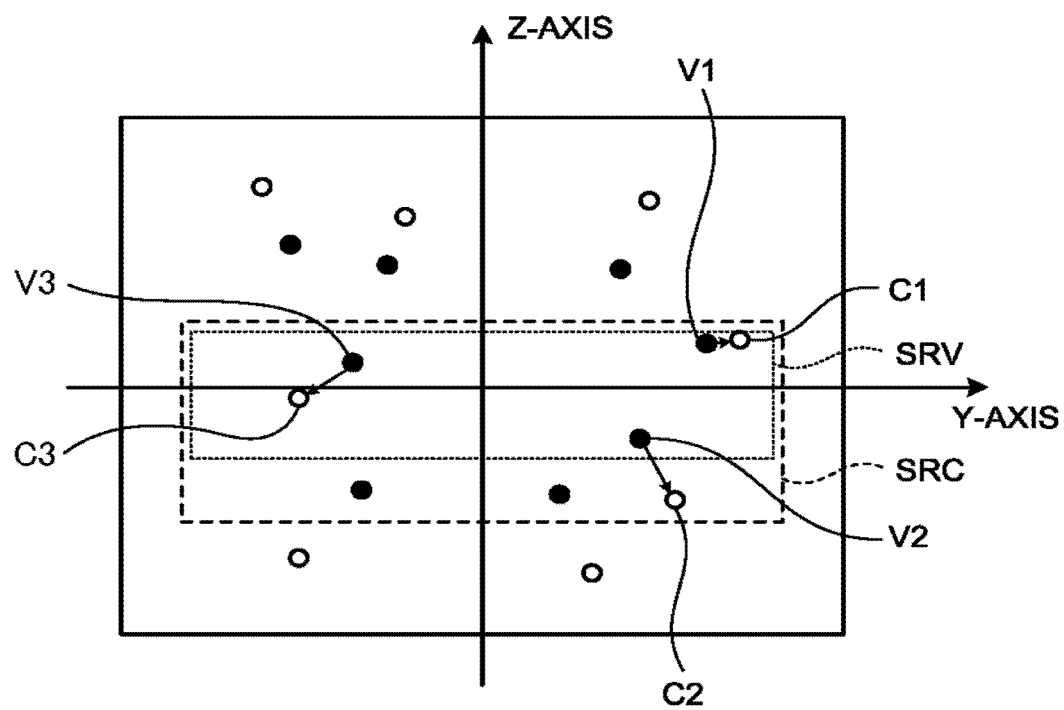
FIG. 8 is an illustrative drawing of exemplary matching processing performed by a position matching function according to the first embodiment.

The position matching function 37b matches a landmark detected by the detecting function 37a on volume data of the subject with a landmark on the above-described virtual patient image using identification codes and associates the coordinate space of the volume data and the coordinate space of the virtual patient image with each other. FIG. 8 is an illustrative drawing of exemplary matching processing performed by the position matching function 37b according to the first embodiment. In FIG. 8, the matching processing is performed between three pairs of landmarks, each pair of which is matched using identification codes indicative of identical landmarks and assigned for a landmark detected from a scanogram and a landmark detected from a virtual patient image; however, the embodiment is not limited to this case. The matching processing may be performed between any number of pairs of landmarks.

For example, as illustrated in FIG. 8, when matching the landmarks indicated by the identification codes "V1", "V2", and "V3" on a virtual patient image with the landmarks indicated by the identification codes "C1", "C2", and "C3" on a scanogram, the position matching function 37b transforms the coordinates to minimize a positional difference between identical landmarks and associates coordinate spaces of the respective images with each other. For example, as illustrated in FIG. 8, the position matching function 37b calculates the following coordinate transformation matrix "H" in a manner minimizing "LS", the total amount of positional differences between respective pairs of same anatomical landmarks such as "V1 (x1, y1, z1), C1 (X1, Y1, Z1)", "V2 (x2, y2, z2), C2 (X2, Y2, Z2)", and "V3 (x3, y3, z3), C3 (X3, Y3, Z3)".

$$LS=((X1,Y1,Z1)-H(x1,y1,z1))+((X2,Y2,Z2)-H(x2,y2,z2))+((X3,Y3,Z3)-H(x3,y3,z3))$$

Figure 9:
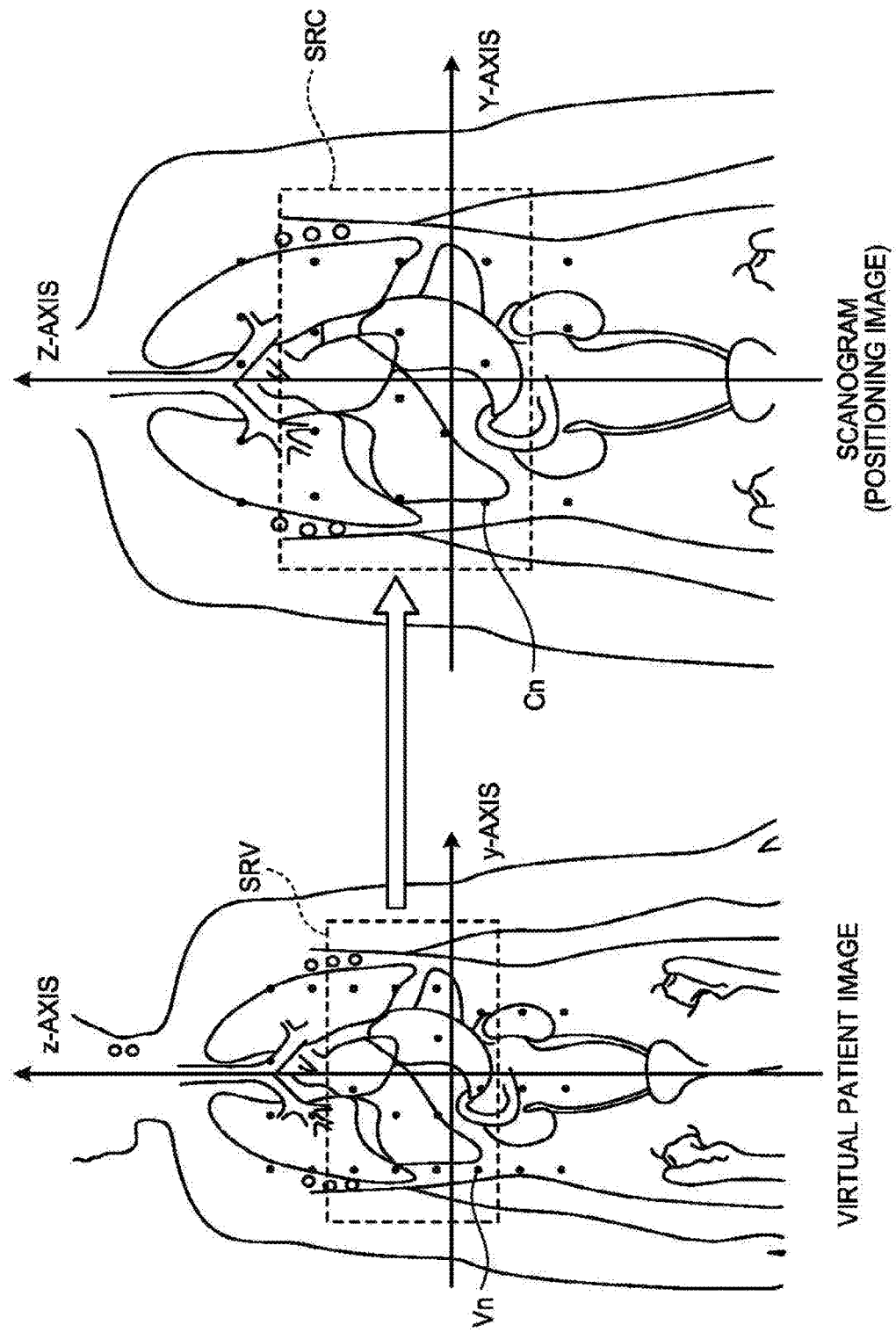
FIG. 9 is a drawing to illustrate exemplary transformation of scanning ranges using coordinate transformation according to the first embodiment.

The position matching function 37b is capable of transforming a scanning range designated on the virtual patient image to a scanning range on the positioning image using the calculated coordinate transformation matrix "H". For example, as illustrated in FIG. 8, the position matching function 37b is capable of transforming the scanning range "SRV" designated on the virtual patient image to the scanning range "SRC" on the positioning image using the coordinate transformation matrix "H". FIG. 9 is a drawing to illustrate exemplary transformation of scanning ranges using coordinate transformation according to the first embodiment. For example, as illustrated on the virtual patient image of FIG. 9, when an operator sets the scanning range "SRV" on the virtual patient image, the position matching function 37b transforms the set scanning range "SRV" to the scanning range "SRC" on the scanogram using the above-described coordinate transformation matrix.

With this process, the scanning range "SRV" set in a manner including a landmark corresponding to an identification code "Vn" on the virtual patient image is transformed to the scanning range "SRC" including an identification code "Cn" corresponding to the same landmark on the scanogram and is set in this state. The above-described coordinate transformation matrix "H" may be stored in the storage 35 for each subject and read out for use as appropriate or may be calculated on each collection of a scanogram. In this manner, according to the first embodiment, by displaying a virtual patient image for designation of a range in presetting and by planning a position and a range on the image, a position and a range on a positioning image corresponding to the planned position and range can be automatically numerically set after imaging of the positioning image (scanogram).

Referring back to illustration of FIG. 2, the processing circuitry 37 includes the receiving function 37c and the estimating function 37d and provides control for taking an image in desired image quality by a simple operation. The operation will be later described in detail.

As a conventional manner for obtaining consistent image quality on a reconstruction image, the x-ray dose is controlled such that the standard deviation (SD) of noise on the reconstruction image is maintained at a certain value. This control, however, may fail to maintain image quality on the reconstruction image.

Use of the iterative reconstruction, which is being widely introduced, is an exemplary case of failing to maintain image quality of a reconstruction image. With a conventional X-ray CT device, when the SD (designated SD) maintained constant is set at 10, the device calculates the tube current such that the SD is close to 10 regardless of whether the imaged body part is a lung field or an abdomen. Application of the iterative reconstruction to this configuration may fail to secure consistent image quality on the reconstruction image. In the iterative reconstruction, the tube current is therefore corrected based on the X-ray count. Correction is decreased for the lung field having a larger count, whereas correction is increased for the abdomen having a smaller count. In this case, increased correction on the abdomen may cause uneven graininess (for example, a coarse grained image may be generated), which is disadvantageous to the image quality.

The X-ray CT device 1 according to the first embodiment therefore includes the following configuration that allows imaging of an image having desired image quality by a simple operation.

For each body part, the storage 35 stores information in which a plurality of image quality levels are associated with the respective X-ray doses detected by the detector 13 in a plurality of views used for reconstruction of an image in each image quality level. In other words, the storage 35 stores information pieces relating to a plurality of body parts, a plurality of image quality levels for each of the information pieces relating to body parts, and information relating to a first X-ray count value corresponding to each of the image quality levels in an associated manner. The storage 35 is an example of a memory unit.

FIG. 10 is a drawing to illustrate exemplary information stored in the storage 35 according to the first embodiment. For example, the storage 35 stores information for an abdomen in which an image quality level, a count, and a benchmark image are associated with one another. The image quality level is information indicating the image quality of a reconstruction image. As an example of the image quality level, the storage 35 stores information indicating any of "low dose", "standard", "quality", and "high quality" in the order from the lower image quality to the higher image quality. The count (the count value) is an X-ray dose detected by the detector 13 in a plurality of views used for reconstruction of an image in a certain image quality level. For example, the storage 35 stores a count value of electric charge accumulated in the X-ray detecting elements through a plurality of views as an X-ray count. The benchmark image is an image serving as a benchmark of image quality in each body part and corresponding to each image quality level. As an example of the benchmark image, an image is registered the image quality level of which allows a diagnosis without increasing radiation exposure of the subject P. For example, the storage 35 stores a reconstruction image of a certain sectional surface (for example, a coronal plane) on the abdomen of a phantom or the subject P as a benchmark image. FIG. 10 illustrates exemplary information stored for an abdomen; however, information pieces about other body parts such as a head and a lung field are similarly stored. The count illustrated in FIG. 10 is preliminarily registered in the storage 35 by an operator based on the count of data obtained by conventional two-dimensional scanography, three-dimensional scanography, or the like.

The image quality level is determined by at least one of factors including the noise power spectra (NPS) representing graininess, the modulation transfer function (MTF) representing resolution, the size of the object, the attenuation of the object, the contrast, and an artifact. The image quality level may be determined by a plurality of factors including SD of noise on the reconstruction image. For example, the image quality level is determined by the SD and at least one of factors including the NPS, the MTF, the size of the object, the attenuation of the object, the contrast, and an artifact.

As illustrate in FIG. 10, for example, the storage 35 stores information in which "low dose" as the image quality level, "a" as the count, and "A" as the benchmark image are associated with one another. The storage 35 further stores information in which "standard" as the image quality level, "b" as the count, and "B" as the benchmark image are associated with one another. The storage 35 further stores information in which "quality" as the image quality level, "c" as the count, and "C" as the benchmark image are associated with one another and stores information in which "high quality" as the image quality level, "d" as the count, and "D" as the benchmark image are associated with one another. The above-described information pieces stored in the storage 35 are preliminarily registered in the storage 35 by an operator or the designer of the X-ray CT device 1.

It should be noted that FIG. 10 is merely an example. In the above-described example, the storage 35 stores four different image quality levels; however, the embodiment is not limited to this configuration. The storage 35 may store any number of image quality levels or store a single image quality level (for example, stores only "standard"). In another case, instead of storing an image itself as the benchmark image, the storage 35 may store information indicating a place (a link destination) to store the image.

The receiving function 37c receives an operation to designate an image quality level for a body part included in the imaging range from an operator. For example, when the operator creates an imaging plan, the receiving function 37c receives an operation to designate an image quality level for each body part included in the imaging range on a virtual patient image. In other words, the receiving function 37c selects a desired body part and an image quality level corresponding to the desired body part. The receiving function 37c is an example of a receiving unit or a selecting unit.

Figure 11:
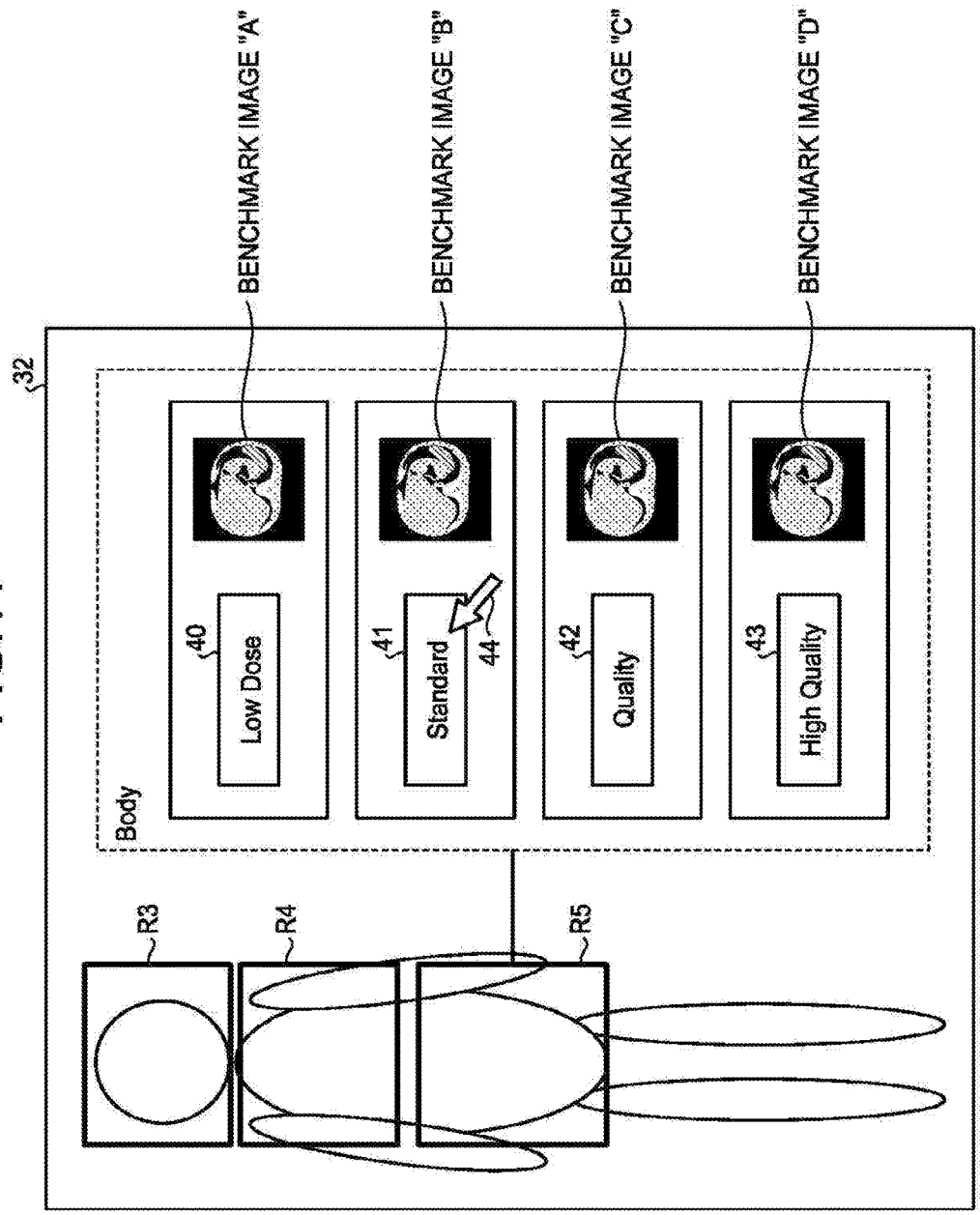
FIG. 11 is a drawing to illustrate an example of an imaging plan creation screen according to the first embodiment.

FIG. 11 is a drawing to illustrate an example of an imaging plan creation screen according to the first embodiment. Specifically, FIG. 11 illustrates an example of an imaging plan creation screen displayed on the display 32 when an imaging plan is created on a virtual patient image.

As illustrated in FIG. 11, for example, when an instruction to start creation of an imaging plan is input to the input circuit 31 by an operator, the processing circuitry 37 displays images corresponding to respective image quality levels on the display 32. More specifically, the processing circuitry 37 displays a virtual patient image on the left side of the screen and displays regions R3 to R5 for creating imaging plans. The region R3 corresponds to the head, and the region R4 corresponds to the lung field, and the region R5 corresponds to the abdomen. When the region R5 for the abdomen is selected by the operator, the processing circuitry 37 acquires a plurality of image quality levels corresponding to the abdomen and benchmark images corresponding to the respective image quality levels from the storage 35 and displays a selection field (in the dashed line in FIG. 11) for selecting an image quality level based on the acquired information. The selection filed includes, for example, a button 40 for designating "low dose", a button 41 for designating "standard", a button 42 for designating "quality", and a button 43 for designating "high quality" as image quality levels. A benchmark image "A", a benchmark image "B", a benchmark image "C", and a benchmark image "D", which correspond to the respective image quality levels, are displayed on the right sides of the respective buttons 40 to 43. For example, when the operator operates a cursor 44 and presses the button 41, the receiving function 37c receives designation of "standard" as the image quality level.

FIG. 11 is merely an example. For example, the benchmark images "A" to "D" are not necessarily displayed. Of the benchmark images "A" to "D", only the benchmark image "B" corresponding to the image quality level "standard" may be displayed.

The estimating function 37d estimates the X-ray dose emitted on a body part, of a plurality of body parts, based on the amount of X-ray detected by the detector 13 such that predetermined image quality is obtained on the reconstruction image of the body part included in the imaging range of the main imaging performed after the positioning imaging. In other words, the estimating function 37d acquires information relating to a second tube current used in the main imaging based on information relating to the first tube current, information relating to a second X-ray count in the positioning imaging, and information relating to a first X-ray count associated with the selected image quality level. The estimating function 37d is an example of an estimating unit or an acquiring unit.

For example, the estimating function 37d acquires a detected amount corresponding to the image quality level of a body part received by the receiving function 37c from the storage 35. The estimating function 37d thereafter estimates the X-ray dose emitted on the body part in the main imaging based on the acquired detected amount, the X-ray dose emitted on the body part in the positioning imaging, and the detected amount of X-ray transmitted through the body part and detected by the detector 13 in the positioning imaging.

More specifically, when the receiving function 37c receives an image quality level of the body part, the estimating function 37d acquires a count corresponding to the received image quality level with reference to information stored in the storage 35. The estimating function 37d thereafter estimates a tube current for generating X-rays emitted on the body part in the main scanning based on the acquired count, a tube current having generated the X-rays emitted on the body part in the scanography, and the count of X-rays transmitted through the body part and detected by the detector 13 in the scanography. For example, the estimating function 37d estimates a tube current used in the main scanning using the following formula (1).

$$\text{a tube current in main scanning} = \text{a tube current in scanography} \times \text{a count of a benchmark image} / \text{a count in scanography} \quad (1)$$

In the formula (1), a tube current in main scanning represents a tube current for generating X-rays emitted on the body part in main scanning. A tube current in scanography represents a tube current having generated X-rays emitted on the body part in scanography. The tube current in scanography can be acquired from, for example, an imaging plan for the scanogram. A count in scanography represents a count value of electric charge accumulated in the X-ray detecting elements in a plurality of views used for reconstruction of the scanogram. The count in scanography can be obtained by, for example, counting the number of electric charges accumulated in the X-ray detecting elements in the views in the scanography and recording the number. A count of a benchmark image represents a count of X-rays transmitted through the body part in imaging of the benchmark image and detected by the detector 13, and the count corresponds to a count obtained from the storage 35.

Figure 12:
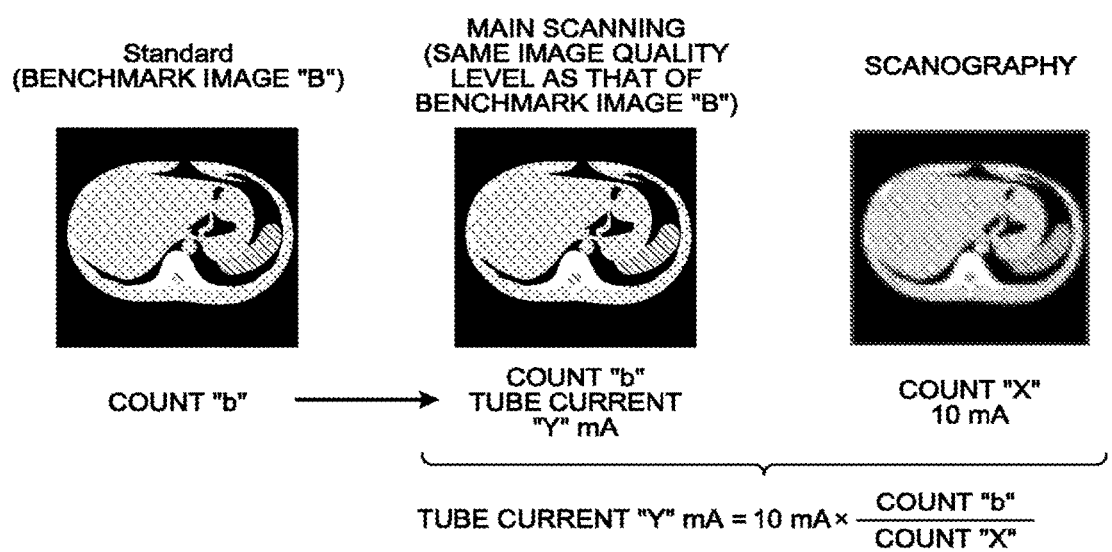
FIG. 12 is an illustrative drawing of processing performed by an estimating function according to the first embodiment.

FIG. 12 is an illustrative drawing of processing performed by the estimating function 37d according to the first embodiment. FIG. 12 illustrates exemplary processing content of the estimating function 37d when the receiving function 37c receives an operation to designate "standard" as the image quality level for the abdomen. In the example of FIG. 12, the tube current estimated by the estimating function 37d is "Y" mA, the tube current used in scanography is 10 mA, and the count of X-rays in the scanography is "X".

As illustrated in FIG. 12, when the receiving function 37c receives an operation to designate "standard" as the image quality level, the estimating function 37d acquires "b" as a count corresponding to "standard" with reference to information (FIG. 10) stored in the storage 35. The estimating function 37d estimates the tube current "Y" mA by substituting the acquired count "b", the count "X", and the tube current 10 mA into the above-described formula (1). Specifically, the estimating function 37d obtains the tube current "Y" mA by calculating "the tube current 10 mA×the count "b"/the count "X"" as illustrated in FIG. 12. The formula for calculating the tube current "Y" mA is merely an example, and in another case, any correction coefficient may be used based on imaging conditions and the like.

In this manner, the estimating function 37d estimates the X-ray dose to be emitted. In the above description, the X-ray dose emitted on the abdomen is estimated. In another case, when a plurality of body parts (for example, the lung field and the abdomen) are included in the imaging range in main imaging, tube currents for respective body parts may be estimated. The estimating function 37d estimates the X-ray dose emitted on each body part included in the imaging range from among a plurality of body parts.

Furthermore, in the above-described example, the count of scanography is counted in the scanography and recorded; however, the embodiment is not limited thereto. For example, the estimating function 37d may calculate the count from projection data of a scanogram. As an example, the estimating function 37d provides inverse transformation for the processing that has already been performed by the data acquisition system 14 and the preprocessing circuitry 34 on projection data (corrected projection data) stored in the storage 35. With this processing, the estimating function 37*d* calculates detection data (the number of electric charges accumulated in the X-ray detecting elements) of X-rays detected by the detector 13 in each view and calculates the count of scanography by counting (accumulating) the number of electric charges in the views necessary for reconstruction of the scanogram. The estimating function 37*d* performs processing that transforms projection data collected in the scanography to the amount of X-ray detected by the detector 13 in the scanography and calculates the amount of X-ray detected by the detector 13 on the body part in the scanography. In other words, the estimating function 37*d* calculates information relating to the second X-ray count value detected by the detector in positioning imaging from projection data collected in the positioning imaging. The estimating function 37*d* thereafter estimates the dose in main imaging using the calculated X-ray detected amount and a detection amount for obtaining certain image quality.

Figure 13:
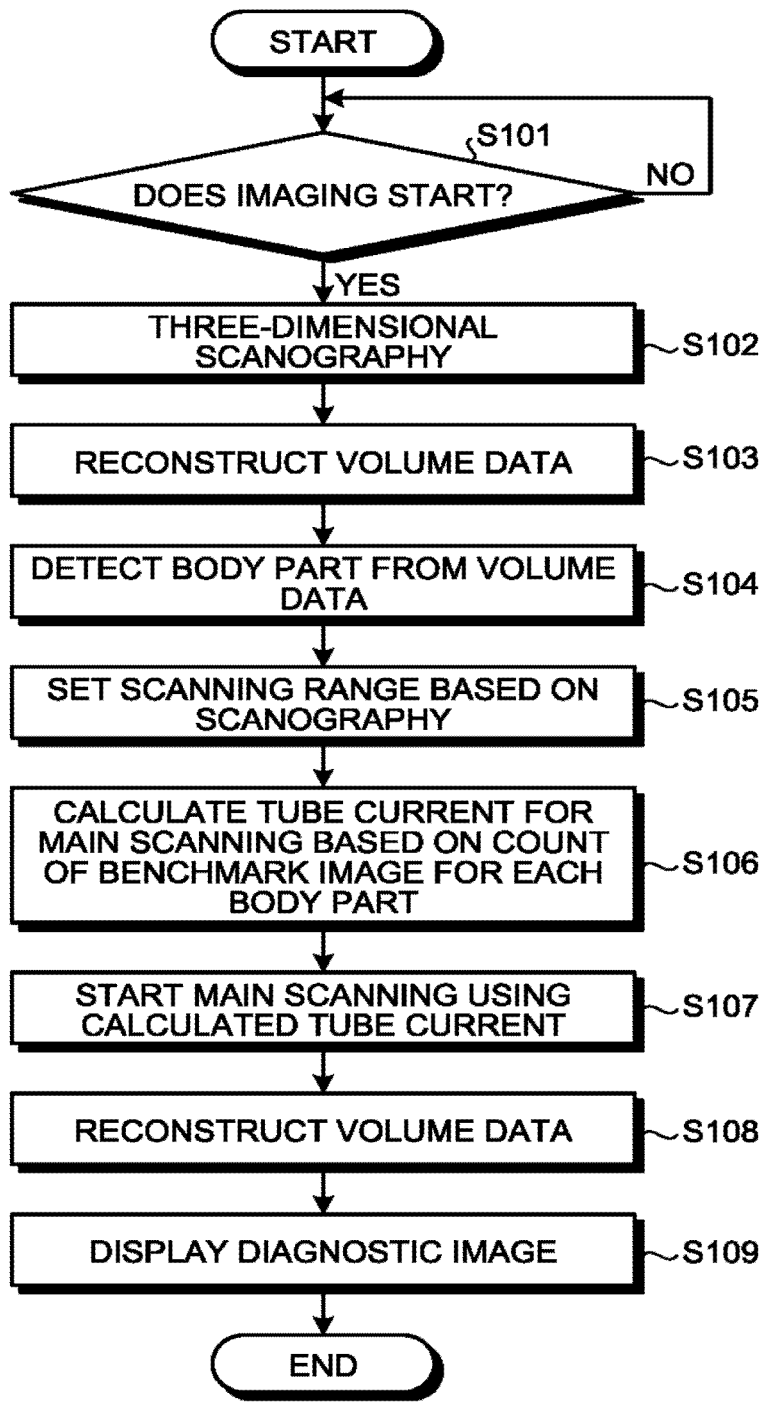
FIG. 13 is a flowchart to illustrate a processing procedure performed by the X-ray CT device according to the first embodiment.

FIG. 13 is a flowchart to illustrate a processing procedure performed by the X-ray CT device 1 according to the first embodiment. The processing of FIG. 13 is performed in accordance with an imaging plan created by an operator. Designation of an image quality level received by the receiving function 37*c* is reflected on the imaging plan carried out by the processing of FIG. 13.

Step S101 is a step corresponding to the scanning control circuitry 33. At Step S101, the scanning control circuitry 33 starts imaging. In the case of no at Step S101, the scanning control circuitry 33 does not start imaging and stays in the standby state.

Step S102 is a step corresponding to the scanning control circuitry 33. In the case of yes at Step S101, the scanning control circuitry 33 images a three-dimensional scanogram (three-dimensional scanography) at Step S102.

Step S103 is a step corresponding to the image reconstruction circuitry 36. At Step S103, the image reconstruction circuitry 36 reconstructs volume data from projection data collected in the three-dimensional scanography.

Step S104 is a step corresponding to the detecting function 37*a*. At this step, the processing circuitry 37 reads a processing program corresponding to the detecting function 37*a* from the storage 35 and executes the program, whereby the detecting function 37*a* is implemented. At Step S104, the detecting function 37*a* detects a plurality of body parts of a subject from reconstructed volume data.

Step S105 is a step corresponding to the input circuit 31. At Step S105, the input circuit 31 receives an operation to set a scanning range based on the three-dimensional scanography.

Step S106 is a step corresponding to the estimating function 37*d*. At this step, the processing circuitry 37 reads a processing program corresponding to the estimating function 37*d* from the storage 35 and executes the program, whereby the estimating function 37*d* is implemented. At Step S106, the estimating function 37*d* calculates a tube current used in main scanning based on the count of a benchmark image for each body part detected by the detecting function 37*a*.

Step S107 is a step corresponding to the scanning control circuitry 33. At Step S107, the scanning control circuitry 33 starts main scanning using the calculated tube current. In other words, the scanning control circuitry 33 serving as a control unit controls the X-ray tube to start main imaging based on the acquired second tube current.

Step S108 is a step corresponding to the image reconstruction circuitry 36. At Step S108, the image reconstruction circuitry 36 reconstructs volume data from projection data collected in the main scanning.

Step S109 is a step corresponding to the processing circuitry 37. At Step S109, the processing circuitry 37 displays a diagnostic image created based on the reconstructed volume data on the display 32.

It should be noted that FIG. 13 is merely an example. For example, the above-described processing procedure is not necessarily performed in the above-described order. Steps S101 to S109 may be performed in another order as appropriate in a manner without causing inconsistency in the processing content.

As described above, in the X-ray CT device 1 according to the first embodiment, the receiving function 37*c* receives an operation to designate an image quality level for a body part included in the imaging range from an operator. The estimating function 37*d* estimates the X-ray dose emitted on the body part based on the amount of X-ray detected by the detector 13 such that predetermined image quality is obtained on the reconstruction image of the body part included in the imaging range of the main imaging out of a plurality of body parts detected from the positioning image. This configuration allows the X-ray CT device 1 to take an image in desired image quality by a simple operation.

Figure 14:
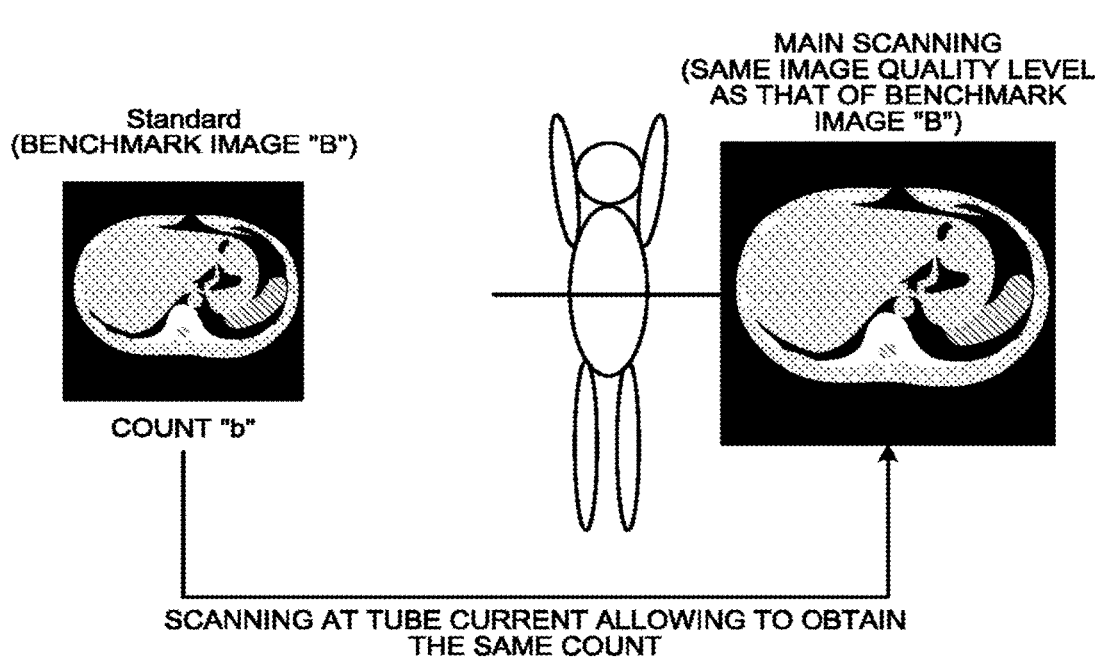
FIG. 14 is an illustrative drawing of an effect of the X-ray CT device according to the first embodiment.

FIG. 14 is an illustrative drawing of an effect of the X-ray CT device 1 according to the first embodiment. As illustrated in FIG. 14, the receiving function 37*c* receives an operation to designate an image quality level for a body part to be imaged from an operator. For example, in this process, upon designation of "standard" as the image quality level, the estimating function 37*d* estimates such a tube current that allows the same count as the count "b" corresponding to the image quality level "standard" to be obtained. The scanning control circuitry 33 performs main scanning using the tube current estimated by the estimating function 37*d*. With this process, the X-ray CT device 1 can reconstruct an image having the same image quality as that of the benchmark image "B" corresponding to the image quality level "standard". In other words, the operator only has to select a desired image quality level at the step of creating the imaging plan to obtain a reconstruction image in the selected image quality level. Additionally, appropriate selection of a desired image quality level results in taking images without setting tube voltage higher than necessary, which can reduce radiation exposure of the subject P.

To prevent selection of an image quality level higher than necessary, the processing circuitry 37 may display an index (a numerical value) according to the image quality level. For example, a computed tomography dose index (CTDI) according the image quality level of a benchmark image may be stored as an index, and the processing circuitry 37 may display the CTDI along with the benchmark image. The index is not limited to the CTDI, and examples of the index may include a value serving as an index of the dose, any value determined by the medical facility, and a value used for information in a diagnosis. When the operator selects the image quality level, the processing circuitry 37 may display an index according to the image quality level instead of displaying a benchmark image.

The estimating function 37*d* estimates a dose (the tube voltage) necessary for obtaining an image having desired image quality using the count of electric charge detected in a plurality of views used for image reconstruction. The X-ray CT device 1 can remove effects of processing performed by the data acquisition system 14 and the preprocessing circuitry 34 in estimating the X-ray dose, which can improve accuracy in the estimation.

Different Embodiment

Various different embodiments may be applied other than the above-described embodiment.

Preset of Image Quality Level

In the above-described embodiment, the operator performs an operation to designate an image quality level; however, the embodiments are not limited to this manner. For example, the operator does not necessarily designate an image quality level when a desired image quality level is preset for each imaging plan.

FIG. 15 is an illustrative drawing of preset of an image quality level according to a different embodiment. In the example of FIG. 15, three imaging plans are preset that include "whole body: standard", "whole body: low dose", and "whole body: quality" as imaging plans for taking images of the head, the lung field, and the abdomen. In this example, "quality" for the image quality level of the head, "low dose" for the image quality level of the lung field, and "standard" for the image quality level of the abdomen are preset in the imaging plan "whole body: standard". Similarly, "quality" for the image quality level of the head, "low dose" for the image quality level of the lung field, and "low dose" for the image quality level of the abdomen are preset in the imaging plan "whole body: low dose". Furthermore, "high quality" for the image quality level of the head, "standard" for the image quality level of the lung field, and "quality" for the image quality level of the abdomen are preset in the imaging plan "whole body: quality".

The operator can therefore obtain an image of appropriate image quality only by selecting any imaging plan from the three imaging plans including "whole body: standard", "whole body: low dose", and "whole body: quality". Additionally, for example, the operator can perform reset to optionally change the image quality levels for a certain body part after selecting any imaging plan.

Reregistration of a Benchmark Image

Addition of a new function to the processing performed by the data acquisition system 14 and the preprocessing circuitry 34 can change the relation between a count and image quality of a benchmark image stored in the storage 35. In this case, the X-ray CT device 1 can update the count and the benchmark image using a simulator.

Figure 16:
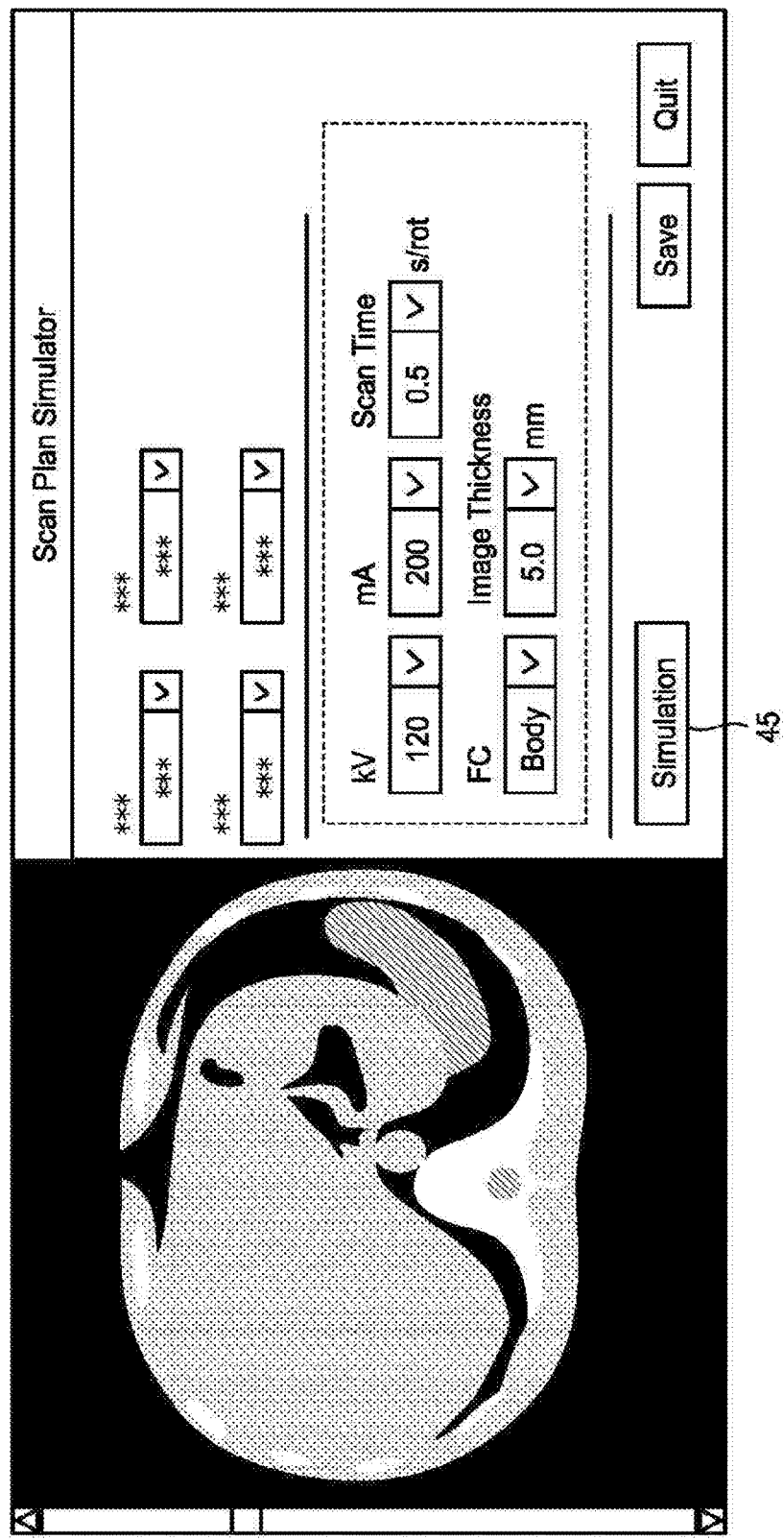
FIG. 16 is an illustrative drawing of reregistration of a benchmark image according to the different embodiment.

FIG. 16 is an illustrative drawing of reregistration of a benchmark image according to the different embodiment. FIG. 16 illustrates an exemplary screen of a simulator used by the X-ray CT device 1. As illustrated in FIG. 16, various kinds of parameters such as the tube voltage, the tube current, the scan time, functions (FC), and the image thickness can be input to the simulator.

Implementation of a new function on the data acquisition system 14 and the preprocessing circuitry 34 may improve the image quality of a reconstruction image. In other words, image quality may be improved even with the same count. The X-ray CT device 1 therefore simulates how much the image quality of a benchmark image stored in the storage 35 can be improved.

Specifically, the processing circuitry 37 acquires a count stored in the storage 35, inputs the acquired count and various kinds of parameters to the simulator, and generates a reconstruction image reconstructed upon implementation of the new function.

The reconstruction image generated by the simulator may have higher image quality than that of the original benchmark image. The operator therefore compares the generated reconstruction image with the original benchmark image. When the generated reconstruction image has higher image quality than that of the original benchmark image, the same level of image quality as that of the original benchmark image may be secured with a count smaller than the count currently stored in the storage 35. The processing circuitry 37 thereafter simulates how much the count is decreased when the image quality of the reconstruction image generated in the simulation is decreased to the same image quality level as that of the original benchmark image.

In this process, the processing circuitry 37 inputs a smaller count than the count stored in the storage 35 and has another simulation. The processing circuitry 37 repeats the operations and acquires a count of when a reconstruction image having the same image quality as that of the original benchmark image has been generated. The processing circuitry 37 updates the count stored in the storage 35 with the count acquired by the simulator.

In this manner, the processing circuitry 37 can simulate a count that allows the same image quality level to be obtained when a new function is implemented. In another case, the processing circuitry 37 may update the benchmark image with the reconstruction image generated by the simulator. The image reconstruction circuitry 36 generates a reconstruction image based on projection data acquired in main imaging. When the image quality level of the reconstruction image is higher than that of the image, the storage 35 updates the image with the reconstruction image and stores the updated image.

Figure 17:
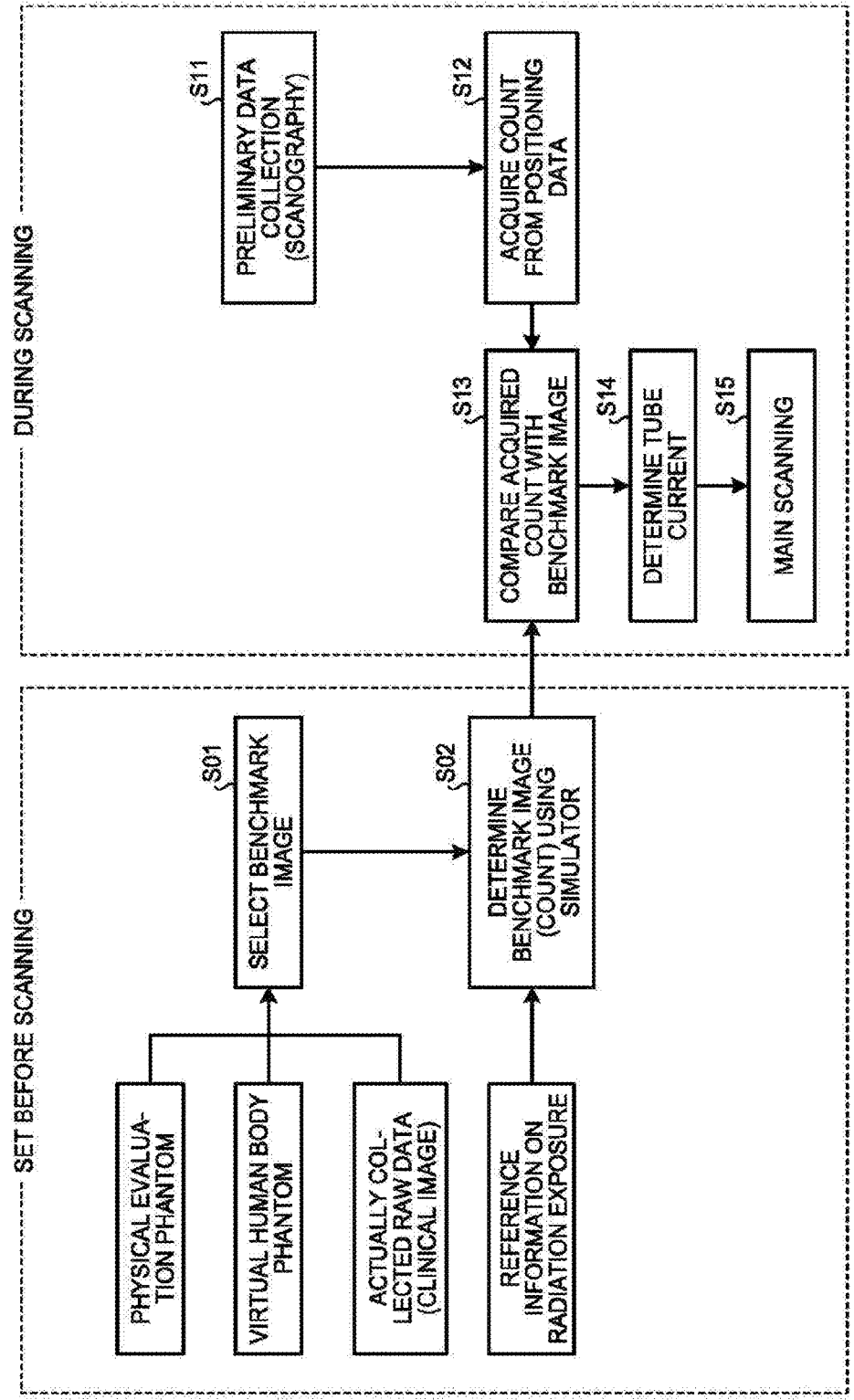
FIG. 17 is an illustrative drawing of a benchmark image according to the embodiment.

A benchmark image will now be described with reference to FIG. 17. FIG. 17 is an illustrative drawing of a benchmark image. As described in the first embodiment, in scanning the subject P, the X-ray CT device 1 performs preliminary data collection (scanography) (S11) and acquires a count from positioning data (S12). The X-ray CT device 1 thereafter compares the acquired count with a benchmark image (S13) and determines a tube current based on the result (S14). The X-ray CT device 1 performs main scanning using the determined tube current (S15).

For example, the benchmark image compared with the count is set by the operator before scanning. For example, the operator selects any data from a phantom for physical evaluation (a scanned image), a virtual human body phantom (a scanned image), and actually collected raw data (such as a clinical image collected in a medical facility) as benchmark data (S01). The operator thereafter determines a benchmark image (a count) using a simulator (S02). The operator, for example, determines a benchmark image with reference to information on radiation exposure corresponding to the benchmark data. With this process, the operator can generate a benchmark image used in the facility, for example, by performing a simulation using actually collected raw data with raw noise added thereto.

Application to Two-dimensional Imaging

In the above-described embodiments, positioning imaging and main imaging are performed in three dimensions; however, the embodiments are not limited thereto. For example, the embodiments are applicable to collection of two-dimensional images (or positioning images) in two-dimensional positioning imaging and main imaging.

Medical Information Management Device

Furthermore, in the embodiments, each function relating to the embodiments is included in the X-ray CT device 1; however, the embodiments are not limited thereto. For example, the detecting function 37a, the position matching function 37b, the receiving function 37c, and the estimating function 37d illustrated in FIG. 2 may be included in a medical information management device connected to the X-ray CT device 1.

Figure 18:
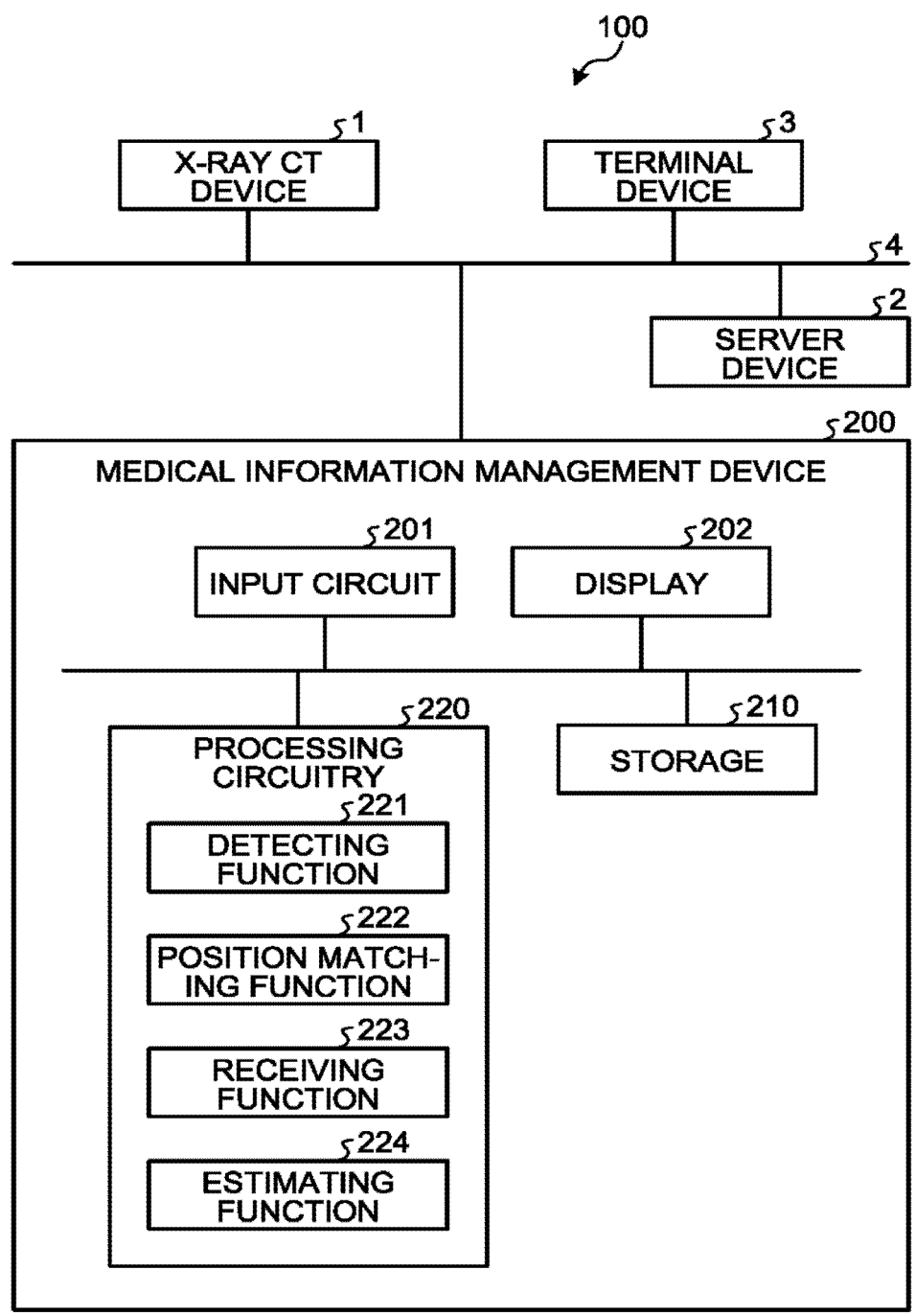
FIG. 18 is a drawing to illustrate an exemplary configuration of a medical information management device according to the different embodiment.

FIG. 18 is a drawing to illustrate an exemplary configuration of the medical information management device according to the different embodiment. The configuration in FIG. 18 has a medical information management device 200 included in the medical information processing system 100 illustrated in FIG. 1.

The medical information management device 200 is a computer functioning to set conditions for imaging performed by a plurality of medical image diagnostic devices such as the X-ray CT device 1, an X-ray diagnostic device, and a magnetic resonance imaging (MRI) device and to interpret the images. The medical information management device 200 illustrated in FIG. 18 controls the X-ray CT device 1 to perform positioning imaging and main imaging. The medical information management device 200 is capable of receiving positioning images and diagnostic images taken by the X-ray CT device 1 and displaying the images on a display 202 and is further capable of various image processing. The medical information management device 200 may be equipped in a medical facility such as a hospital or may be equipped out of the facility.

As illustrated in FIG. 18, the medical information management device 200 includes an input circuit 201, a display 202, storage 210, and processing circuitry 220. The input circuit 201 and the display 202 basically have the same configurations of the input circuit 31 and the display 32 illustrated in FIG. 2, and description thereof will be omitted.

The storage 210 stores positioning images and diagnostic images received from the X-ray CT device 1. The storage 210 stores results of processing performed by the later-described processing circuitry 220 as appropriate. The storage 210 further stores information pieces relating to a plurality of body parts, a plurality of image quality levels for each information piece relating to a body part, and information relating to a first X-ray count value corresponding to each image quality level in a manner associated with one another.

The processing circuitry 220 is a processor controlling imaging performed by a plurality of medical image diagnostic devices. For example, the processing circuitry 220 controls the scanning control circuitry 33 of the X-ray CT device 1 and controls CT scanning performed in the gantry 10. The processing circuitry 220 controls the image reconstruction circuitry 36 of the X-ray CT device 1 and controls image reconstruction processing and image generation processing performed by the console 30. The processing circuitry 220 controls the display 202 to display various kinds of image data stored in the storage 210.

The processing circuitry 220 executes a detecting function 221, a position matching function 222, a receiving function 223, and an estimating function 224 as illustrated in FIG. 18. For example, the detecting function 221, the position matching function 222, the receiving function 223, and the estimating function 224 illustrated in FIG. 18 basically execute the same processing of the detecting function 37a, the position matching function 37b, the receiving function 37c, and the estimating function 37d illustrated in FIG. 2.

The detecting function 221 serving as a detecting unit detects a plurality of body parts of a subject included in a positioning image collected through positioning imaging performed at the first tube current. The receiving function 223 serving as a selecting unit selects a desired body part and an image quality level corresponding to the desired body part. The estimating function 224 serving as an acquiring unit acquires information relating to a second tube current used in main imaging based on information relating to the first tube current, information relating to the second X-ray count value in positioning imaging, information relating to the first X-ray count value associated with the selected image quality level. The processing circuitry 220 serving as a transmitting unit transmits the acquired information relating to the second tube current to the X-ray CT device 1. With this configuration, the medical information management device 200 controls the X-ray CT device 1 to perform main imaging using the second tube current.

The case illustrated in FIG. 18 is merely an example and is not intended to limit the embodiment. For example, the medical information management device 200 may include the preprocessing circuitry 34 and the image reconstruction circuitry 36 illustrated in FIG. 2. In this case, the medical information management device 200 receives projection data collected through positioning imaging and projection data collected through main imaging from the X-ray CT device 1. The medical information management device 200 thereafter reconstructs a positioning image or a diagnostic image from the respective received projection data pieces.

In FIG. 2, processing functions executed by the detecting function 37a, the position matching function 37b, the receiving function 37c, and the estimating function 37d are implemented by a single processing circuitry 37. Instead of this configuration, a processing circuit may be established by combining a plurality of independent processors, and the functions may be implemented with the respective processors executing the programs.

The word "processor" in the above description is indicative of a circuit such as a central processing unit (CPU), a graphics processing unit (GPU), an application specific integrated circuit (ASIC), a programmable logic device (such as a simple programmable logic device (SPLD)), a complex programmable logic device (CPLD), and a field programmable gate array (FPGA). The processor implements a function by reading a program stored in storage and executing the program. Instead of storing a program in the storage, the program may be directly embedded in a circuit of the processor. In this configuration, the processor implements a function by reading the program embedded in the circuit and executing the program. Each processor in the embodiment is not necessarily configured as a single circuit. A plurality of independent circuits may be combined together to configure a processor and implement the functions. A plurality of components in FIG. 2 may be integrated into a single processor and may implement the functions.

Components of each device are illustrated as functional ideas and are not therefore necessarily physically configured as illustrated in the drawings. Forms of separation and integration of the devices are not limited to those illustrated in the drawings, and the whole of or a part of the devices can be configured in a manner functionally or physically separated from or integrated with one another in any unit based on various kinds of load and conditions of use. Moreover, the whole of or a part of the processing function implemented by each device may be implemented by a CPU or a program analyzed and executed by the CPU or may be implemented as hardware using a wired logic.

In each processing described in the embodiments, the whole of or a part of the processing described as automatically executed processing may be manually executed, and conversely, the whole of or a part of the processing described as manually executed processing may be automatically executed by a known method. Moreover, the processing procedures, the control procedures, the names, and information including various kinds of data and parameters set forth in the above description and drawings may be changed in any manner except cases particularly mentioned.

The methods of control described in the embodiments can be implemented by having a computer such as a personal computer and a workstation execute a prepared control program. The methods of control can be distributed through a network such as the Internet and can be executed by being recorded in a computer-readable memory medium such as a hard disk, a flexible disc (FD), a CD-ROM, an MO, and a DVD and being read from the memory medium by a computer.

According to at least an embodiment described above, an image in desired image quality can be taken by a simple operation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT device comprising:
an X-ray tube;
a detector configured to detect a transmitted X-ray emitted from the X-ray tube and transmitted through a subject;
image reconstruction circuitry configured to, in positioning imaging performed at a first tube current, reconstruct a positioning image from projection data collected based on a detection signal of the transmitted X-ray from the detector;
storage configured to store information pieces relating to a plurality of body parts of the subject, a plurality of image quality levels for each of the information pieces relating to the body parts, and information relating to a first X-ray count value corresponding to each of the image quality levels in an associated manner; and
processing circuitry configured to detect a plurality of body parts of the subject included in the positioning image, select a desired body part and an image quality level corresponding to the desired body part, acquire information relating to a second tube current in main imaging based on information relating to the first tube current, information relating to a second X-ray count value in the positioning imaging, and information relating to the first X-ray count value associated with the selected image quality level, and control the X-ray tube to execute the main imaging based on the acquired second tube current.

2. The X-ray CT device according to claim 1, wherein
the storage further stores a plurality of benchmark images respectively corresponding to the plurality of image quality levels, and
the processing circuitry displays at least one of the benchmark images on a display.

3. The X-ray CT device according to claim 2, wherein
the image reconstruction circuitry generates a reconstruction image based on projection data acquired in the main imaging, and
when an image quality level of the reconstruction image is higher than an image quality level of the stored benchmark image, the storage updates the stored benchmark image with the reconstruction image.

4. The X-ray CT device according to claim 1, wherein the processing circuitry calculates information relating to the second X-ray count value detected by the detector in the positioning imaging from the projection data collected in the positioning imaging.

5. The X-ray CT device according to claim 1, wherein, out of the body parts, for each body part included in an imaging range of the main imaging, the processing circuitry acquires information relating to the second tube current of an X-ray emitted on the body part.

6. The X-ray CT device according to claim 1, wherein the image quality level is defined by a degree for at least one of a plurality of factors including a noise power spectra representing graininess, a modulation transfer function representing resolution, a size of an object, attenuation of an object, a contrast, and an artifact.

7. The X-ray CT device according to claim 1, wherein the image quality level is defined by a degree for standard deviation of noise on a reconstruction image.

8. A medical information management device comprising:
storage configured to store information pieces relating to a plurality of body parts of a subject, a plurality of image quality levels for each of the information pieces relating to the body parts, and information relating to a first X-ray count value corresponding to each of the image quality levels; and
processing circuitry configured to detect a plurality of body parts of the subject included in a positioning image collected in positioning imaging performed at a first tube current, select a desired body part and an image quality level corresponding to the desired body part, acquire information relating to a second tube current in main imaging based on information relating to the first tube current, information relating to a second X-ray count value in the positioning imaging, and information relating to the first X-ray count value associated with the selected image quality level, and transmit the acquired information relating to the second tube current to an X-ray CT device.

* * * * *